United States Patent [19]

Harlan et al.

[11] Patent Number: 5,718,883
[45] Date of Patent: Feb. 17, 1998

[54] TRANSGENIC ANIMAL MODEL FOR AUTOIMMUNE DISEASES

[75] Inventors: David M. Harlan, Potomac; Carl H. June, Rockville, both of Md.

[73] Assignee: The United States of America as represented by the Secretary of the Navy, Washington, D.C.

[21] Appl. No.: 197,790

[22] Filed: Feb. 17, 1994

Related U.S. Application Data

[63] Continuation-in-part of Ser. No. 48,042, Apr. 14, 1993, abandoned.

[51] Int. Cl.$^6$ ............................................. A61K 49/00
[52] U.S. Cl. ........................... 424/9.2; 435/172.3; 800/2; 800/DIG. 1; 514/2
[58] Field of Search ............................ 536/235, 24.1; 424/9; 435/172.1, 172.3, 240.1, 240.2, 320.1; 800/2, DIG. 1; 935/6, 11, 59, 70; 514/2

[56] References Cited

U.S. PATENT DOCUMENTS

| 4,736,866 | 4/1988 | Leder et al. | 800/1 |
| 5,175,383 | 12/1992 | Leder et al. | 800/2 |

FOREIGN PATENT DOCUMENTS

| WO 92/00092 | 1/1992 | WIPO |
| WO 92/06187 | 4/1992 | WIPO |

OTHER PUBLICATIONS

P Lomedico et al (1979) Cell 18:545–558.

MB Soares et al (1985) Mol Cell Biol 5:2090–2103.

Guerder et al (1994) Proc Natl Acad Sci USA 91:5138–5142.

J Kuby (1994) Immunology pp. 75–77.

Goodman (1984) In Basic and Clinical Immunology, Stiles et al, eds, p. 21.

Harlan et al., (1994), "Mice expressing both B7–1 and viral glycoprotein on pancreatic beta cells along with glycoprotein–specific transgenic T cells develop diabetes due to a breakdown of T–lymphocyte unresponsiveness", *Proceedings of the National Academy of Science*, vol. 91, pp. 3137–3141.

Hathcock et al., (1993), "Indentification of an Alternative CTLA–4 Ligand Costimulatory for T Cell Activation", *Science*, vol. 262, pp. 905–907.

Freeman et al., (1993), "Uncovering of Functional Alternative CTLA–4 Counter–Receptor in B7–Deficient Mice", *Science*, vol. 262, pp. 907–909.

Gimmi et al., (1993), "Human T–cell clonal anergy is induced by antigen presentation in the absence of B7 costimulation", *Proceedings of the National Academy of Sciences*, vol. 90, pp. 6586–6590.

Tan et al., (1993), "Induction of Alloantigen–specific Hyporesponsiveness in Human T Lymphocytes by Blocking Interaction of CD28 with Its Natural Ligand B7/BB1", *J. Exp. Med.*, vol. 177, pp. 165–173.

Freeman, G. J., et al., (1993), "Murine B7–2, an Alternative CTLA4 Counter–receptor that Costimulates T Cell Proliferation and Interleukin 2 Production", *The Journal of Experimental Medicine*, vol. 178, pp. 2185–2192.

Freeman, G. J., (1993), "Cloning of B7–2: A CTLA–4 Counter–Receptor That Costimulates Human T Cell Proliferation", *Science*, vol. 262, pp. 909–911.

Azuma et al., (1993), "B70 antigen is a second ligand for CTLA–4 and CD28", *Nature*, vol. 366, pp. 76–79.

(List continued on next page.)

*Primary Examiner*—Bruce R. Campell
*Attorney, Agent, or Firm*—A. David Spevack; Amy E. Mandragouras; Lahive & Cockfield, LLP

[57] ABSTRACT

A transgenic animal, whose germ cells and somatic cells contain a transgene including a DNA sequence encoding a CD28 ligand and a tissue-specific promoter operably linked to the DNA sequence, wherein the tissue-specific promoter effects expression of the CD28 ligand in cells of a specific tissue of the animal is disclosed. This animal serves as a transgenic model for specific autoimmune diseases.

19 Claims, 11 Drawing Sheets

OTHER PUBLICATIONS

Baskar et al., (1993), "Constitutive expression of B7 restores immunogenicity of tumor cells expressing truncated major histocompatability complex class II molecules", *Proceedings of the National Academy of Sciences*, vol. 90, pp. 5687–5690.

Townsend, S. E., and Allison, J. P., (1993), "Tumor Rejection After direct Costimulation of $CD8^+T$ Cells by B7–Transfected Melanoma Cells", *Science*, vol. 259, pp. 368–370.

Stewart et al., (1993), "Induction of Type I Diabetes by Interferon–α in Transgenic Mice", *Science*, vol. 260, pp. 1942–1946.

Ohashi et al., (1993), "Induction of Diabetes Is Influenced by the Infectious Virus and Local Expression of MHC Class I and Tumor Necrosis Factor–α", *Journal of Immunology*, vol. 150, No. 11, pp. 5185–5194.

Wogensen et al., (1993), "Leukocyte Extravasation into the Pancreatic Tissue in Transgenic Mice Expressing Interleukin 10 in the Islets of Langerhans", *J. Exp. Med.*, vol. 178, pp. 175–185.

Azuma et al., (1993), "Functional Expression of B7/BB1 on Activated T Lymphocytes", *J. Exp. Med.*, vol. 177, pp. 845–850.

Sansom, and Hall, (1993), "B7/BB1, the ligand for CD28, is expressed on repeatedly activated human T cells in vitro", *Eur. J. Immunol.*, vol. 23, No. 1, pp. 205–298.

Harding et al., (1992), "CD28–mediated signalling co–stimulates murine T cells and prevents induction of anergy in T–cells clones", *Nature*, vol. 356, pp. 607–609.

Higuchi et al., (1992), "Expression of a tumor Necrosis Factor α Transgene in Murine Pancreatic β Cells Results in Severe and Permanent Insulitis without Evolution towards Diabetes", *J. Exp. Med.*, vol. 176, pp. 1719–1731.

Chen et al., (1992), "Costimulation of Antitumor Immunity by the B7 Counterreceptor for the T Lymphocyte Molecules CD28 and CTLA–4", *Cell*, vol. 71, pp. 1093–1102.

Picarella et al., (1992), "Insulitis in transgenic mice expressing tumor necrosis factor β (lymphotoxin) in the pancreas", *Proceedings of the National Academy of Science*, vol. 89, pp. 10036–10040.

Burtles et al., (1992), "Absence of T Cell Tolerance to Pancreatic Islet Cells", *The Journal of Immunology*, vol. 149, No. 6, pp. 2185–2193.

Herold et al., (1992), "Induction of Tolerance to Autoimmune Diabetes with Islet Antigens", *J. Exp. Med.*, vol. 176, pp. 1107–1114.

Heath et al., (1992), "Autoimmune diabetes as a consequence of locally produced interleukin–2", *Nature*, vol. 359, pp. 547–549.

Allison et al., (1992), "Inflammation but not autoimmunity occurs in transgenic mice expressing constitutive levels of interleukin–2 in islet β cells", *Eur. J. Immunol.*, vol. 22, pp. 1115–1121.

Cheng et al., (1992), "Cachexia and graft–vs.–host–disease–type skin changes in keratin promoter–driven TNFα transgenic mice", *Genes & Development*, vol. 6, pp. 1444–1456.

D'Armiento et al., (1992), "Collagenase Expression in the Lungs of Transgenic Mice Causes Pulmonary Emphysema", *Cell*, vol. 71, pp. 955–961.

Du Bois et al., (1992), "T–Lymphocytes that Accumulate in the Lung in Sarcoidosis Have Evidence of Recent Stimulation of the T–Cell Antigen Receptor", *Amer. Rev. Resp. Dis.*, vol. 145, pp. 1205–1211.

Fink et al., (1992), "Immunologic Aspects of Granulomatous and Interstitial Lung Diseases and of Cystic Fibrosis", *JAMA*, vol. 268, No. 20, pp. 2874–2881.

Freeman et al., (1992), "CTLA–4 and CD28 mRNA are coexpressed in most T cells after activation", *The Journal of Immunology*, vol. 149, No. 12, pp. 3795–3801.

Gow et al., (1992), "Myelin Basic Protein Gene Contains Separates Enhancers for Oligodendrocyte and Schwann Cell Expression", *J. Cell. Biol.*, vol. 119, No. 3, pp. 605–616.

Guerder et al., (1992), "Role of Expression of T Cell Costimulators on Perenchymal Tissue in the Development of Autoimmunity?", *J. Cell. Biochem. Supp. Keystone Symposia on Mollecular & Cellular Biology*, Abstract # 0 321, p. 48.

Hauft et al., (1992), "Expression of SV–40 T Antigen in the Small Intestinal Epithelium of Transgenic Mice Results in Proliferative Changes in the Crypt and Reentry of Villus–associated Enterocytes into the Cell Cycle but Has No Apparent Effect on Cellular Differentiation Programs and Does Not Cause Neoplastic Transformation", *J. Cell. Biol.*, vol. 117, No. 4, pp. 825–839.

Ledent et al., (1992), "Thyroid expression of an $A_2$ adenosine receptor transgene induces thyroid hyperplasia and hyperthyroidism", *EMBO Journal*, vol. 11, No. 2, pp. 537–542.

Lee et al., (1992), "Glucagon Gene 5'–Flanking Sequences Direct Expression of Simian Virus 40 Large T Antigen to the Intestine, Producing Carcinoma of the Large Bowel in Transgenic Mice", *J. Biol. Chem.*, vol. 267, No. 15, pp. 10705–10708.

Reiser et al., (1992), "Murine B7 antigen provides an efficient costimulatory signal for activation of murine T lymphocytes via the T–cell receptor/CD3 complex", *Proceedings of the National Academy of Science*, vol. 89, pp. 271–275.

Strober et al., (1992), "Immunopathogenesis of Gastrointsetinal and Hepatobiliary Diseases", *JAMA*, vol. 268, No. 20, pp. 2910–2917.

Vanderberghe et al., (1992), "In situ expression of B7/BB1 on antigen presenting cells and activated B cells: an immunohistochemical study", *Int. Immunol.*, vol. 5, No. 3, pp. 317–321.

Wispe et al., (1992), "Human Mn–Superoxide Dismutase in Pulmonary Epithelial Cells of Transgenic Mice Confers Protection from Oxygen Injury", *J. Biol. Chem.*, vol. 267, No. 33, pp. 23937–23941.

Zweiman et al., (1992), "Immunologic Aspects of Neurological and Neuromuscular Diseases", *JAMA*, vol. 268, No. 20, pp. 2918–2922.

Linsley et al., (1991), "Binding of the B Cell Activation Antigen B7 to CD28 Costimulates T Cell Proliferation and Interleukin 2 mRMA Accumulation", *J. Exp. Med.*, vol. 173, pp. 721–730.

Gimmi et al., (1991), "B–cell surface antigen B7 provides a costimulatory signal that induces T cells to proliferate and secrete interleukin 2", *Proceedings of the National Academy of Sciences*, vol. 88, pp. 6575–6579.

Freeman et al., (1991), "Structure, Expression, and T Cell Costimulatory Activity of the Murine Homologue of the Human B Lymphocyte Activation Antigen B7", *J. Exp. Med.*, vol. 174, pp. 625–631.

Ohashi et al., (1991), "Ablation of Tolerance and Induction of Diabetes by Virus Infection in Viral Antigen Transgenic Mice", *Cell*, vol. 65, pp. 305–317.

Weide, L. G., and Lacy P. E., (1991), "Low-Dose Streptozocin-Induced Autoimmune Diabetes in Islet Transplantation Model", *Diabetes*, vol. 40, pp. 1157–1162.

Kamradt et al., (1991), "Pertussis Toxin Prevents the Induction of Peripheral T Cell Anergy and Enhances the T Cell Response to an Encephalitogenic Peptide of Myelin Basic Protein", *J. Immunol.*, vol. 147, No. 10, pp. 3296–3302.

June et al., (1991), "Signal transduction in T cells", *Curr. Op. Immunol.*, vol. 3, pp. 287–293.

Roth et al., (1991), "Use of transgenic mice to infer the biological properties of small intestinal stem cells and to examine the lineage relationships of their descendants", *Proceedings of the National Academy of Science*, vol. 88, pp. 9407–9411.

Roman et al., (1990), "The Expression of Influenza Virus Hemagglutinin in the Pancreatic β Cells of Transgenic Mice Result in Autoimmune Diabetes", *Cell*, vol. 61, pp. 383–396.

Götz et al., (1990), "Non-tolerance and differential susceptibility to diabetes in transgenic mice expressing major histocompatability class II genes on pancreatic β cells", *Eur. J. Immunol.*, vol. 20, pp. 1677–1683.

Burkly et al., (1990), "Tolerance in Transgenic Mice Expressing Major Histocompatability Molecules Extrathymically on Pancreatic Cells", *Science*, vol. 248, pp. 1364–1368.

June et al., (1990), "Role of the CD28 receptor in T-cell activation", *Immunology Today*, vol. 11, No. 6, pp. 211–216.

Miller et al., (1990), "Tissue-specific Expression of Allogeneic Class II MHC Molecules Induces Neither Tissue Rejection Nor Clonal Inactivation of Alloreactive T Cells", *J. Immunol.*, vol. 144, No. 1, pp. 334–341.

Miller et al., (1990), "Transgenic Models of T-Cell Self Tolerance and Autoimmunity", *Immunol. Rev.*, vol. 118, pp. 21–35.

Sarvetnick et al., (1990), "Loss of pancreatic islet tolerance induced by β-cell expression of interferon-γ", *Nature*, vol. 346, pp. 844–847.

Siegel et al., (1990), "Mechanisms of Autoimmunity in the Context of T-Cell Tolerance: Insights from Natural and transgenic Animal Model Systems", *Immunol. Rev.*, vol. 118, pp. 165–192.

Schwartz et al., (1990), "A Cell Culture Model for T Lymphocyte Clonal Anergy", *Science*, vol. 248, pp. 1349–1356.

Freeman et al., (1989), "B7, A New Member of the Ig Superfamily with Unique Expression on Activated and Neoplastic B Cells", *The Journal of Immunology*, vol. 143, No. 8, pp. 2714–2722.

Böhme et al., (1989), "Transgenic Mice with I-A on Islet Cells Are Normoglycemic But Immunologically Intolerant", *Science*, vol. 244, pp. 1179–1183.

Morahan and Miller, (1989), "Tolerance of class I histocompatability antigens expressed extrathymically", *Nature*, vol. 339, pp. 622–624.

Lo et al., (1988), "Diabetes and Tolerance in Transgenic Mice Expressing Class II MHC Molecules in Pancreatic Beta Cells", *Cell*, vol. 53, pp. 159–168.

Allison et al., (1988), "Diabetes in transgenic mice resulting from over-expression of class I histocompatability molecules in pancreatic β cells", *Nature*, vol. 333, pp. 529–533.

Sarvetnick et al., (1988), "Insulin-Dependent Diabetes Mellitus Induced in Trangenic Mice by Ectopic Expression of Class II MHC and Interferon-Gamma", *Cell*, vol. 52, pp. 773–782.

Markman et al., (1988), "Antigen presenting function of class II MHC expressing pancreatic beta cells", *Nature*, vol. 336, pp. 475–479.

Freedman, A. S., et al., (1987), "B7, A B Cell-restricted Antigen That Indentifies Preactivated B Cells", *The Journal of Immunology*, vol. 139, No. 10, pp. 3260–3267.

Adams et al., (1987), "Non-tolerance and autoantibodies to a transgenic self antigen expressed in pancreatic β cells", *Nature*, vol. 325, pp. 223–228.

Yokochi et al., (1982), "B Lymphoblast Antigen (BB1) Expressed on Epstein-Barr Virus-Activated B Cell Blasts, B Lymphoblastoid Cell Lines, and Burkitt's Lymphomas", *J. Immunol.*, vol. 128, No. 2, pp. 823–827.

Rossini et al., (1977), "Studies of streptozotocin-induced insulitis and diabetes", *Proceedings of the National Academy of Science*, vol. 74, pp. 2485–2489.

Like, A. A., and Rossini, A. A., (1976), "Streptozotocin-Induced Pancreatic Insulitis: New Model of Diabetes Mellitus", *Science*, vol. 193, pp. 415–417.

Oehen, S. et al. (1992) "Vaccination or tolerance to prevent diabetes", *European Journal of Immunology*, vol. 22., pp. 3149–3153.

368
+ CONTROL
– CONTROL
PANCREAS
THYMUS
SPLEEN
LIVER
LUNG
KIDNEY
BONE M.
OVARY
HEART
SK. MUS.

378
– CONTROL
+ CONTROL
PANCREAS
THYMUS
BRAIN
SK. MUS.
BONE M.
OVARY
SPLEEN
LUNG
KIDNEY
HEART
LIVER

340
+ CONTROL
– CONTROL
BRAIN
HEART
THYMUS
LIVER
OVARY
PANCREAS
KIDNEY
SK. MUS.
LUNG
BONE M.

FIG. 7A  FIG. 7B  FIG. 7C
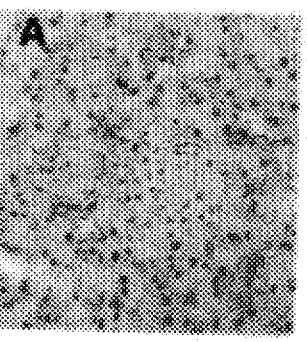 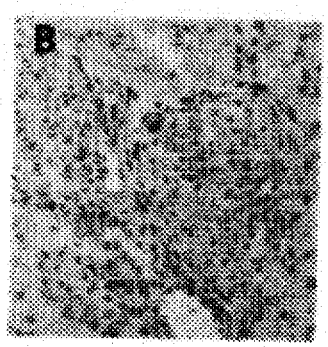 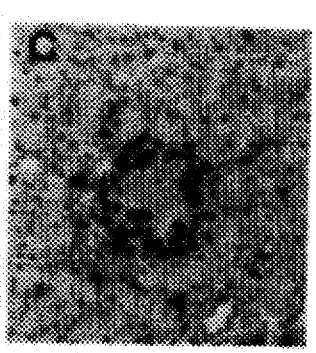
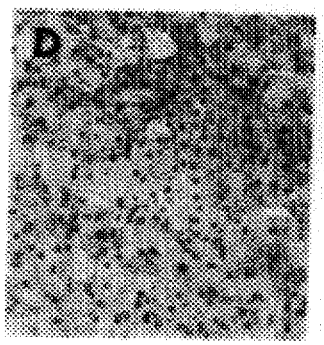  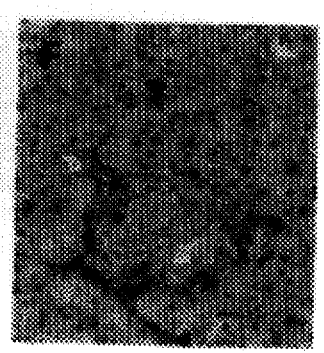
FIG. 7D  FIG. 7E  FIG. 7F FIG. 7G    FIG. 7H    FIG. 7I
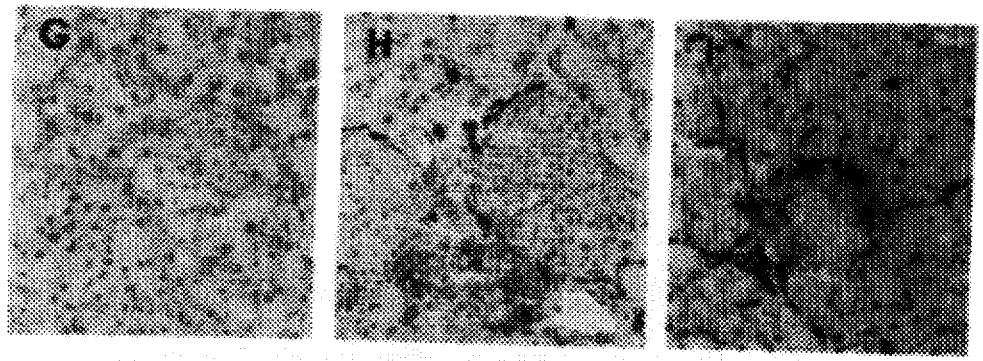
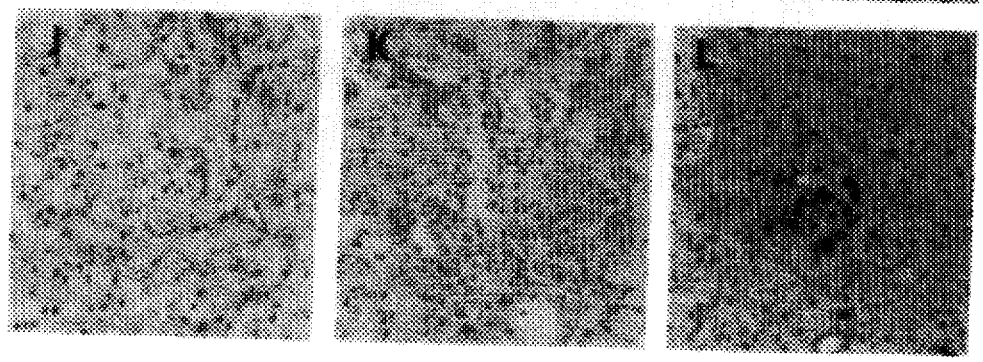
FIG. 7J    FIG. 7K    FIG. 7L 5,718,883

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
( A ) LENGTH: 18
( B ) TYPE: nucleic acid (C) STRANDEDNESS: single
(D) TOPOLOGY: linear (xi) SEQUENCE DESCRIPTION: SEQ ID NO: 1:

TTTCAGCACC GTGCTAGC 18

(2) INFORMATION FOR SEQ ID NO: 2:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO: 2:

ATGCTGGTGC AGCACTGA 18

(2) INFORMATION FOR SEQ ID NO: 3:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO: 3:

CGGTGACCTT CAGACCTT 18

(2) INFORMATION FOR SEQ ID NO: 4:

(i) SEQUENCE CHARACTERISTICS:
(A) LENGTH: 22
(B) TYPE: nucleic acid
(C) STRANDEDNESS: single
(D) TOPOLOGY: linear (xi) SEQUENCE DESCRIPTION: SEQ ID NO: 4:

CAAGCAAGAT GTAGAGTCTG CG 22

(2) INFORMATION FOR SEQ ID NO: 5:

(i) SEQUENCE CHARACTERISTICS:
(A) LENGTH: 21
(B) TYPE: nucleic acid
(C) STRANDEDNESS: single
(D) TOPOLOGY: linear (xi) SEQUENCE DESCRIPTION: SEQ ID NO: 5:

GGCTTTGGAC ATGAACCGCC C 21

(2) INFORMATION FOR SEQ ID NO: 6:

(i) SEQUENCE CHARACTERISTICS:
(A) LENGTH: 30
(B) TYPE: nucleic acid
(C) STRANDEDNESS: single
(D) TOPOLOGY: linear (xi) SEQUENCE DESCRIPTION: SEQ ID NO: 6:

CGAGGATCCT TTAACTGGGT ACACAGCAGG 30

(2) INFORMATION FOR SEQ ID NO: 7:

(i) SEQUENCE CHARACTERISTICS:
(A) LENGTH: 26
(B) TYPE: nucleic acid
(C) STRANDEDNESS: single
(D) TOPOLOGY: linear ( x i ) SEQUENCE DESCRIPTION: SEQ ID NO: 7:

CTGACCTGCA GTTATGAGGA CAGCAC    2 6

( 2 ) INFORMATION FOR SEQ ID NO: 8:

( i ) SEQUENCE CHARACTERISTICS:
  ( A ) LENGTH: 22
  ( B ) TYPE: nucleic acid
  ( C ) STRANDEDNESS: single
  ( D ) TOPOLOGY: linear ( x i ) SEQUENCE DESCRIPTION: SEQ ID NO: 8:

CAAACAACAG CCTTACCTTC GG    2 2

( 2 ) INFORMATION FOR SEQ ID NO: 9:

( i ) SEQUENCE CHARACTERISTICS:
  ( A ) LENGTH: 22
  ( B ) TYPE: nucleic acid
  ( C ) STRANDEDNESS: single
  ( D ) TOPOLOGY: linear ( x i ) SEQUENCE DESCRIPTION: SEQ ID NO: 9:

GCCTCCAAAA CCTACACATC CT    2 2

TRANSGENIC ANIMAL MODEL FOR AUTOIMMUNE DISEASES

RELATED APPLICATION

This application is a continuation-in-part of U.S. Ser. No. 08/048,042 entitled "Transgenic Animal Model for Autoimmune Diseases" filed Apr. 14, 1993, abandoned, the contents of which are incorporated herein by reference.

STATEMENT AS TO FEDERALLY SPONSORED RESEARCH

This invention was made with Government support under U.S. Navy Work Unit No. 63706N B2EW.00095.003.1007, 6370N M0095.004.1412, and 63706N M0095.001.1005. The Government may have certain rights in the invention.

BACKGROUND OF THE INVENTION

A number of autoimmune diseases result from an inappropriate immune response mediated through abnormal T cell activation. An example of such a detrimental immune response is the destruction of pancreatic β cells (insulin producing cells) that occur in Type I (insulin dependent) diabetes mellitus. Eisenbarth, *New Eng. J. Med.*, 314:1360–1368 (1986); Wilson et al., *Ann. Rev. Med.*, 41:497–508 (1990); and Lernmark et al., *Endocrinol. Metabol. Clin. N. Amer.*, 20:589–617 (1991). Type I diabetes is the most severe form of diabetes and occurs most often in children and young adults. Over one million Americans are presently afflicted with this disease. A number of other diseases are thought to be caused by aberrant T cell activation including psoriasis, thyroiditis, sarcoidosis, multiple sclerosis, tropical spastic paraparesis, inflammatory bowel disease (Crohn's and ulcerative colitis), aplastic anemia, and rheumatoid arthritis.

Normal T cell activation, and the aberrant activation which is the cause of the symptoms of these autoimmune diseases, has recently been recognized to require two separate "signals." Schwartz, *Science*, 248:1349–1356 (1990); and June, *Curr. Op. Immunol.* 3:287–293 (1991). The first T cell activation, or stimulation, signal is believed to be provided through the antigen-specific T cell receptor (TCR) /CD3 complex. Recent data suggests that a second stimulation signal is generated through the T cell receptor CD28 and corresponding ligands, such as the surface molecule B7. June et al., *Immunol. Today,* 11:211–216 (1990); and Harding et al., *Nature*, 356:607–609 (1992). Under normal circumstances B7 is expressed on activated B and T lymphocytes, macrophages, and other antigen presenting cells. Freeman et al., *J. Immunol.*, 143:2714–2722 (1989); Azuma et al., *J. Exp. Med.*, 177:845–850 (1993); and Sansom et al., *Eur. J. Immunol.*, 23:295–298 (1993). The more recently reported B7-2 receptor (Hathcock et al., *Science*, 262:905–907 (1993); Freeman et al., *Science*, 262:907–909 (1993); and Freeman et al., *Science*, 262:909–911 (1993), also called B70 (Azuma et al., *Nature*, 366:76–79 (1993)) has also been found only on specialized APCs. Normally, the B7 family of receptors are not expressed on cells that express only MHC class I molecules. Recently, thyroid cells from patients with autoimmune Graves' thyroiditis were reported to reveal specific anti-B7 (B7-1) immunostaining while thyroid cells from normal individuals did not stain (García-Cózar et al., *Immunologia,* 12:32 (abstract) (1993)). In addition, others have found that psoriatic but not unaffected skin keratinocytes stain with the BB-1 antibody which stains a B7-like molecule (Nickoloff et al., *Am. J. Pathol.*, 142:1029–1040 (1993)). These reports indicate that cells other than conventional APCs can express B7-like molecules. More importantly, these studies have shown that epithelial cells do express a B7-like molecule in some T cell mediated autoimmune states.

While it is well accepted that Type I diabetes results from the gradual immune-mediated destruction of pancreatic β cells, the exact factors responsible for initiating the destructive process remain obscure. It is known from epidemiologic study that a genetic predisposition for Type I diabetes exists, and that disease susceptibility is tightly linked with major histocompatibility complex (MHC) class II genes. Todd, *Immunol. Today*, 11:122–129 (1990). However, disease concordance in identical twins is only 50%, which indicates that genetics can not fully explain the pathophysiology of Type I diabetes.

The mechanism of autoimmune responses in Type I diabetes has been studied by the use of transgenic technology. Burkly et al., *Science*, 248:1364–1368 (1990); Miller et al., *Immunol. Rev.*, 118:21–35 (1990); and Siegel et al., *Immunol. Rev.*, 118:165–192 (1990). For example, several transgenic models have been designed to test pancreatic overexpression of the surface molecule MHC class I, see e.g., Allison et al., *Nature*, 333:529–533 (1988) and Morahan et al., *Nature*, 339:622–624 (1989); pancreatic expression of MHC class II, Lo et al., *Cell*, 53:159–168 (1988), Markmann et al., *Nature*, 336:475–479 (1988), Bohme et al., *Science*, 244:1179–1183 (1989), and Miller et al., *J. Immunol.*, 144:334–341 (1990); and pancreatic expression of tumor necrosis factor β, Picarella et al., *PNAS USA,* 89:10036–40 (1992). However, none of these models has reproduced the immune destruction of β cells seen in Type I diabetes.

Other transgenic mouse models have been created in which exogenous viral antigens are expressed on pancreatic β cells. These studies have reproduced some, but not all, of the characteristics of Type I diabetes. See e.g., Ohashi et al., *Cell*, 65:305–317 (1991); Adams et al., *Nature*, 325:223–228 (1987); and Roman et al., *Cell*, 61:383–396 (1990).

Non-transgenic animal models for Type I diabetes, such as the NOD (non-obese diabetic) mouse model, see, e.g., Kanazawa et al., *Diabetologia,* 27:113–115 (1984), also exist. However, the exact defect underlying the animals' propensity for the disease remains obscure. While much has been learned about the genetic susceptibility of the NOD mouse to develop diabetes, Leiter et al., *Immunol. Today,* 11:147–149 (1990); Parham, *Nature*, 345:662–664 (1990); and Faustman et al., *Science*, 254:1756–1761 (1991), a full understanding of the loss of self-tolerance which results in islet cell destruction remains elusive.

In addition to Type I diabetes, there are numerous other autoimmune diseases caused by a similar loss of self-tolerance. For example, the interaction of epidermal cells and cells of the immune system (T-lymphocytes and neutrophils) is thought to play a central pathophysiologic role in psoriasis, which affects over 2 million individuals in the United States. Nickoloff, *Arch. Dermatol.*, 127:821–826 (1991). It was recently shown that PMA treated keratinocytes express B7-like molecules that serve a co-stimulatory role in T cell activation. Augustin et al., *J. Invest. Dermatol.*, 100:275–281 (1993).

Autoimmune thyroid diseases such as Graves' disease (hyperthyroidism) and Hashimoto's disease (hypothyroidism) are also common, and affect between two and four percent of the population in developed countries with inadequate intake of iodine. See, e.g., McGregor, *O. J.*

Med., 82:1–13 (1992); and Baker, JAMA, 268:2899–2903 (1992). In these diseases, T cell infiltration of the thyroid gland is a predominant histologic feature. It has been suggested that such diseases are caused by a disturbance of immunoregulatory mechanisms mediated by thyroid cells. Volpe, Autoimmunity, 13:3–9 (1992).

Sarcoidosis is a multi-system granulomatous disorder characterized by the accumulation of large numbers of T lymphocytes in affected tissues, primarily in the lungs. DuBois et al., Amer. Rev. Resp. Dis., 145:1205–1211 (1992) and Fink et al., JAMA, 268:2874–2881 (1992). Further, these T lymphocytes display structural and functional evidence of recent activation. A recent report demonstrated that the epithelioid histocytes of a sarcoid involved lymph node stain brightly for B7/BB-1. Vandenberghe et al., Int. Immunol., 5:317–321 (1993).

Multiple sclerosis (MS) is a demyelinating disease involving scattered areas of the white matter of the central nervous system. While the underlying pathophysiologic mechanism of MS remains unknown, recent data suggests an immune pathogenesis. Dhib-Jabut et al., Annals Allergy, 64:433–444 (1990) and Zweiman et al., JAMA, 268:2918–2922 (1992). For example, activated lymphocytes and macrophages are found in lesions of the central nervous system of MS patients. Further, a disease state which shares many characteristics with MS, experimental autoimmune encephalomyelitis (EAE), can be induced in laboratory mice by inducing an immune response against myelin with complete Freund's adjuvant. Swanborg, Methods Enzymol., 162:413 (1988) and McCarron et al., J. Immunol., 147:3296–3302 (1991).

Tropical spastic paraparesis (TSP) is a disease with similarities to MS such as inflammation and demyelination of the white matter. HTLV-1 appears to cause many cases of TSP. Further, it is known that B7 expression, Valle et al., Immunol., 69:531 (1990), and the expression of the interleukin-2 gene, McGuire et al., J. Virol., 67:1590–1599 (1993), are up-regulated in HTLV-1-infected T cells.

Inflammatory bowel diseases (IBD), which include both Crohn's disease and ulcerative colitis, are characterized by chronic gastrointestinal tract intimation of unknown cause. It is currently believed that under normal circumstances a state of immune unresponsiveness occurs when antigens are encountered in the intestinal mucosal environment; in patients with IBD this unresponsive immune state does not occur. Strober et al., JAMA, 268:2910–2917 (1992).

Traditional therapies for autoimmune diseases generally treat the symptoms rather than the cause of the disease, because these therapies cannot prevent T cell activation, which starts destructive chain reactions. Drugs, such as steroids and non-steroid anti-inflammatory drugs (NSAIDS), are currently used to ameliorate symptoms, but they do not prevent the progression of the disease. In addition, these drugs can have undesirable side effects. For example, steroids can induce osteoporosis, organ toxicity, diabetes, and Cushnoid features, and can accelerate the cartilage degeneration process and cause so-called post-injection flares for up to 2 to 8 hours. On the other hand, NSAIDS can have gastrointestinal side effects, and increase the risk of agranulocytosis and iatrogenic hepatitis.

Immunosuppressive drugs are also used as another form of therapy, especially in advanced disease stages. However, these drugs suppress the entire body's immune system and often have severe side effects.

Although the characteristic symptoms of many autoimmune diseases are known and the mechanisms of such diseases and general therapeutic agents have been studied, the need exists for reliable and uncomplicated in vivo models to study these various autoimmune diseases, and to assay possible therapeutic agents that are specific for the different autoimmune diseases.

SUMMARY OF THE INVENTION

The invention demonstrates that aberrant expression of ligands of CD28 on specific peripheral cells, under appropriate conditions, results in the breakdown of T lymphocyte tolerance, and that this breakdown in tolerance mimics T lymphocyte-mediated autoimmune diseases such as diabetes mellitus. Based on these discoveries, the invention features a unique transgenic model which is used to study the role of the interaction of the CD28 receptor and its ligands, such as the B7 molecule and B7 polypeptides, in regulating immune responses in specific autoimmune diseases. This model is based on transgenes that include a DNA sequence encoding a ligand for CD28 and a tissue-specific promoter operably linked to the DNA sequence.

In general, the invention features a transgene that includes a DNA sequence encoding a CD28 ligand, e.g., a B7 polypeptide, such as the full length B7 molecule, and a tissue-specific promoter, e.g., a rat-1 insulin promoter, operably linked to the DNA sequence. In particular, the transgene may be a 3.0 kilobase section of plasmid pRIP-B7-IpA (ATCC Designation No. 97412) between restriction sites Sst I and Stu I, as shown in FIG. 1.

The invention also features an animal cell, e.g., from a mammal, and preferably from a rodent, containing such a transgene and expressing a CD28 ligand, such as a B7 polypeptide. This animal cell may be a pancreatic cell, lung tissue cell, keratinocyte, Schwann cell, oligodendrocyte, intestinal epithelial cell, thyroid cell, or hematopoietic cell.

In addition, the invention features a method of using these transgenes to produce transgene animals, e.g., mammals, preferably rodents, which express a CD28 ligand, e.g., a B7 polypeptide, in cells of a specific tissue, by introducing the transgene into an embryonal cell of an animal, and obtaining progeny from that cell, the progeny containing the transgene stably incorporated into the genome and expressing a CD28 ligand in a specific tissue.

The invention also features a transgenic non-human animal, e.g., a mammal, and preferably a rodent, e.g., a mouse, that has cells of a specific tissue which contain such transgenes and express a CD28 ligand encoded by the transgene. The transgenic animals may be bred to produce an animal that is homozygous for the transgene. In particular, the animal may contain a transgene which is a 3.0 kilobase section of plasmid RIP-B7-IpA (ATCC Designation No. 97412) between restriction sites Sst I and Stu I, as shown in FIG. 1. This transgenic animal can be used as a model for a specific human autoimmune disease, depending on the particular promoter used in the transgene.

In particular, the invention features a transgenic non-human animal, whose germ cells and somatic cells contain a transgene including a DNA sequence encoding a CD28 ligand and a tissue-specific promoter operably linked to the DNA sequence, wherein the tissue-specific promoter affects expression of the CD28 ligand in cells of a specific tissue of the animal, the transgene being introduced into embryonal cells of the animal, or an ancestor of the animal.

Another aspect of the invention features a transgenic non-human animal, whose germ cells and somatic cells contain a first transgene including a first DNA sequence encoding a CD28 ligand and a tissue-specific promoter operably linked to the first DNA sequence and a second transgene including a second DNA sequence encoding a foreign polypeptide and a tissue-specific promoter operably linked to the second DNA sequence. The germ cells and somatic cells of this transgenic animal further contain a third transgene comprising a third DNA sequence encoding a T cell receptor specific for the foreign polypeptide. Preferably, the foreign polypeptide is a viral antigen, such as the lymphocytic choriomeningitis viral (LCMV) glycoprotein (GP).

Furthermore, the invention features a method of testing the efficacy of a therapeutic agent for the treatment of a specific autoimmune disease, by evaluating autoimmune disease symptoms of a transgenic animal of the invention, contacting the transgenic animal with the agent, and reevaluating the disease symptoms of the animal, wherein prevention or amelioration of one or more of the symptoms indicates that the agent is efficacious for the treatment of the specific autoimmune disease. For example, the method may include an assay to determine whether pancreatic β cells are being destroyed in the transgenic animal.

This new model can be adapted to study various autoimmune diseases, such as Type I diabetes, psoriasis, thyroiditis, sarcoidosis, multiple sclerosis, tropical spastic paraparesis, aplastic anemia, and inflammatory bowel disease, and to evaluate the efficacy of potential therapeutic agents that block the interaction between the CD28 receptors and its ligands to ameliorate or prevent these diseases.

As used herein, the term "transgene" means a DNA sequence that includes one or more selected DNAs, e.g., encoding one or more ligands for CD28, to be expressed in a transgenic animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, that may be necessary for optimal expression of the selected DNA, all operably linked to the selected DNA, and may include an enhancer sequence.

As used herein, the term "operably linked" means that selected DNA, e.g., encoding a CD28 ligand, is in proximity with a promoter; e.g., tissue-specific promoter, to allow the promoter to regulate expression of the selected DNA. In addition, the promoter is located upstream of the selected DNA in terms of the direction of transcription and translation.

As used herein, the term "tissue-specific promoter" means a DNA sequence that serves as a promoter, i.e., regulates expression of a selected DNA sequence operably linked to the promoter. A tissue-specific promoter effects expression of the selected DNA sequence in specific cells, e.g., hematopoietic cells, or cells of a specific tissue within an animal, e.g., pancreatic β cells. The term also covers so-called "leaky" promoters, which regulate expression of a selected DNA primarily in one tissue, but cause expression in other tissues as well. According to the invention, such expression in tissues other than the specific tissue of interest will not typically impair a model of a specific autoimmune disease. Such promoters also may include additional DNA sequences that are necessary for expression, such as introns and enhancer sequences.

As used herein, the term "transgenic animal" means an animal which includes a transgene that is inserted into an embryonal cell and becomes a part of the genome of the animal which develops from that cell, or an offspring of such an animal. In the transgenic animals described herein, the transgene causes specific tissue cells to express a ligand for CD28, e.g., a B7 polypeptide, on the surface of cells that do not express such CD28 ligands in the wild-type, non-transgenic animals. Transgenic animals which include one or more transgenes in addition to a transgene encoding one or more ligands for CD28 are within the scope of this invention. For example, a double or triple transgenic animal which includes two or three transgenes can be produced. Any animal which can be produced by transgenic technology is included in the invention, although mammals are preferred. Preferred mammals include non-human primates, sheep, goats, horses, cattle, pigs, rabbits, and rodents such as guinea pigs, hamsters, rats, gerbils, and, preferably, mice.

The term "embryonal cells," as used herein, includes embryonic stem (ES) cells and fertilized oocytes.

As used herein, a "CD28 ligand" is any protein or polypeptide that binds to the T cell receptor CD28 and provides a co-stimulatory signal, which along with the TCR/CD3 first signal, results in T cell stimulation. Such ligands include naturally occurring B7, recombinant B7, and any other protein or polypeptide that binds to the CD28 receptor and provides a signal for the co-stimulatory T cell stimulation pathway. As used herein, "stimulation" includes the activation, or up-regulation, as well as downregulation, of T cells. Up-regulation usually results in lymphokine production and T cell proliferation, while down-regulation may include inhibitive or suppressive mechanisms, and even the induction of T cell death.

As used herein, a "B7 polypeptide" is any polypeptide that binds to the T cell receptor CD28 and provides the same or substantially the same co-stimulatory signal for T cell stimulation as the native B7 molecule. The term includes the full length native B7 protein and mutant analogs of B7, as well as polypeptide fragments of the full length B7 protein and analogs, as long as these fragments bind to the CD28 receptor and provide a stimulation signal.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications mentioned herein are incorporated by reference. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 7A–7L are photographs of immunohistologic analysis of islet infiltrating cells stained with monoclonal antibodies specific for CD8 (A–C), CD4 (D–F), macrophages (G–I), or B lymphocytes (J–L). Panels C, F, I, L: diabetic triple transgenic mouse which show an intense infiltrate comprised of macrophages as well as T and B lymphocytes; Panels H, E, B: non-diabetic triple transgenic mouse which show no infiltration by macrophages (H), CD4$^+$ (E) and CD8$^+$ T cells (B). Panels A,D,G,J: GP-TCR mouse.

DETAILED DESCRIPTION OF THE INVENTION

Figure 1:
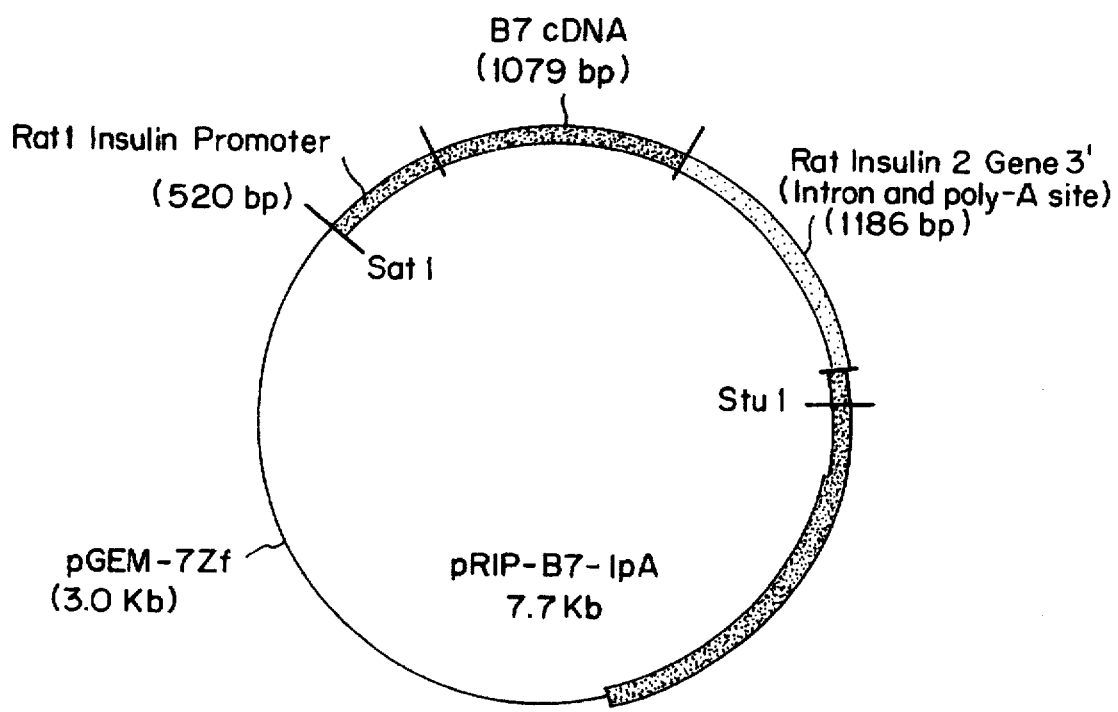
FIG. 1 is a schematic of plasmid pRIP-B7-IpA (ATCC Designation No. 97412).

The invention relates to a transgenic model system to study the role of the interaction of the CD28 receptor and its ligands, e.g., B7, in regulating immune responses in autoimmune diseases. This model uses transgenic animals, such as mice, which are designed to express a CD28 ligand, such as a B7 polypeptide, on specific cells that normally do not express this surface molecule.

When these specific cells express a B7 polypeptide on their surfaces, they provide a co-stimulatory signal to T cells, which they normally lack. As a result, these cells become pseudo-stimulatory cells and, under appropriate conditions, provoke an attack mediated by the T cells which destroys these cells. According to the present invention, this aberrant signaling by specific cells, and resultant destruction of those cells by an animal's immune system is an accurate model for a specific autoimmune disease in the animal.

The general methods for developing transgenic animals which express a CD28 ligand, such as a B7 polypeptide, or different CD28 ligands, on cells of a specific tissue are first described. These transgenic animals allow the study of the genesis and treatment of a number of autoimmune diseases including Type I diabetes, psoriasis, thyroiditis, sarcoidosis, multiple sclerosis, tropical spastic paraparesis, aplastic anemia, and inflammatory bowel disease.

Second, a detailed example of a transgenic Type I diabetes model is described in which a transgenic mouse is made by introducing cDNA that encodes murine B7 into the pancreatic β cells. Type I diabetes symptoms occur in this animal model when β cells acquire the ability to provide the second stimulation signal to β cell-specific T cells via a ligand for CD28, e.g., the B7 molecule. When presented to T cells which have received a primary activation signal (e.g., mediated via the T cell receptor (TCR) following recognition of foreign antigenic peptide presented in the context of the major histocompatibility complex (MHC)) this second stimulation signal (or costimulatory signal) is sufficient to induce an immune response in the animal. A transgenic mouse was created with β cells specifically designed to provide the second signal. Therefore, this mouse model can, under appropriate conditions, be used to study diabetes and to screen potential therapeutic agents which prevent, delay, or ameliorate, the symptoms of Type I diabetes.

Although a transgenic animal may express a CD28 ligand, such as B7, on cells which do not normally express the ligand, the animal may not spontaneously develop an autoimmune disease due to immunologic unresponsiveness. The term immunologic unresponsiveness refers to the uneventful coexistence of antigen-specific T cells in vivo with potential targets, which has generally been attributed to one of three mechanisms occurring alone or in combination: T cell clonal anergy, T cell suppression, and/or the broad category of immune ignorance. Each of these mechanisms of immunologic unresponsiveness is mediated by a different cell type. In clonal anergy, potentially autoreactive T cells are functionally inactivated. Immunologic unresponsiveness due to T cell suppression requires the intervention of a third cell type, i.e., the suppressor cell. In immune ignorance, the cells presenting antigen are either shielded from autoreactive T cells, or provide insufficient stimulation to the T cells.

Immunologic unresponsiveness in a transgenic animal expressing a CD28 ligand, such as B7, on cells which do not normally express the ligand can be overcome by stimulating a primary immune response in the animal. In one embodiment, a primary immune response is stimulated in a transgenic animal by administration of an agent which induces an inflammatory response in the animal. For example, streptozotocin which, in subdiabetogenic doses, is known to induce pronounced pancreatic insulitis, can be administered to a transgenic animal expressing B7 on the surface of pancreatic β cells to stimulate a primary immune response in the animal. Alternatively, an agent known to upregulate cellular expression of MHC class II molecules (e.g., interferon γ (INFγ)), which has been observed in several autoimmune states, can be administered to a transgenic animal expressing a CD28 ligand to overcome immunologic unresponsiveness.

In a preferred embodiment, immunologic unresponsiveness is overcome in a transgenic animal by expressing a CD28 ligand, such as B7, in conjunction with a foreign (i.e., non-native) polypeptide on the surface of a cell which does not normally express the ligand. The presence of the foreign polypeptide in the context of appropriate MHC class II molecules in conjunction with the CD28 ligand provides the necessary primary and secondary signals to T cells to stimulate an immune response. The foreign polypeptide can be any non-native protein or fragment, such as a viral antigen. For example, a transgenic mouse expressing both B7 and a viral glycoprotein, lymphocytic choriomeningitis viral (LCMV) glycoprotein (GP) on pancreatic β cells, and containing T cells expressing the viral-glycoprotein-specific transgenic T cell receptor (TCR) was produced (See Example 2). In these mice, the presence of all three transgenes results in immune mediated destruction of pancreatic β cells.

Other known protocols which can be used to induce diabetes or induce an antigenic stimulation within islets, or a combination thereof can also be used to overcome immunologic unresponsiveness in a transgenic animal expressing a CD28 ligand in pancreatic β cells. Such techniques include, for example, cyclophosphamide treatment (Charlton, *Diabetes*, 38:441 (1989)) perfusion of cytokines known to induce islet damage (e.g., IL-1, INF-γ, TNFα or combinations thereof) and/or increase β cell expression of MHC class II antigens and, thus, the presentation of antigenic peptide (Campbell, *Mol. Endocrinol.*, 2:101 (1982)).

Transgenic Animals That Express a CD28 Ligand in Specific Tissues

Plasmids are constructed by operably linking an appropriate tissue-specific promoter DNA with cDNA encoding a CD28 ligand, such as a B7 polypeptide. In addition, a tissue-specific promoter can be linked to more than one cDNA, each encoding a different CD28 ligand, or a CD28 ligand and some other foreign cell surface antigen. Depending on the specific promoter used, the promoter-cDNA construct may have to be modified using standard techniques to include an intron splice site and/or a polyadenylation signal.

A suitable CD28 ligand can be determined using one of the assays described below, and its cDNA can then be determined by standard techniques. For example, according to the invention, one would link a CD34 promoter with cDNA encoding native B7 to create a model for the study of aplastic anemia. The expression of this promoter-CD28 ligand transgene is then verified by direct detection of ligand expression in appropriate tissue culture cells. For example, full length native B7 cDNA linked to the keratin-14 promoter would be tested for expression of the B7 protein in cultured keratinocytes.

A preferred B7 polypeptide includes a portion of the amino acid sequence corresponding to the extracellular domain of the B7 molecule, i.e., amino acid positions 1 to 215, as described in Freeman et al., *J. Immunol.*, 143:2714–2722 (1989), which describes the cDNA sequence of the complete native B7 molecule, and is incorporated herein by reference. See, also, Linsley et al., WO 92/00092, which is incorporated herein by reference.

The methods of the invention can be used to develop autoimmune models for any disease in which a tissue-specific promoter can be found or developed that regulates expression of the selected CD28 ligand on a specific tissue or cell that is normally afflicted by the autoimmune disease.

Transgenic animals, e.g., mice, rats, monkeys, or goats, are then produced by introducing the promoter-CD28 ligand transgenes into embryonal cells of the animal by standard techniques. In the case of fertilized oocytes, the preferred method of transgene introduction is by microinjection, see, e.g., Leder et al., U.S. Pat. Nos. 4,736,866 and 5,175,383, which are incorporated herein by reference, whereas in the case of embryonic stem (ES) cells, the preferred method is electroporation. However, other methods including viral delivery systems such as retroviral infection, or liposomal fusion can be used.

Thereafter, tissue-specific expression of the CD28 ligand by the transgenes is verified with the assay described below. Some transgenic animals may carry multiple copies of the transgene, with the transgene copies incorporated at different sites in the genome. The site of transgene incorporation into the genome can strongly influence transgene expression; therefore, one may correlate transgene expression with discrete transgene restriction fragment length polymorphism patterns.

In addition, two transgenic animals, each expressing a different CD28 ligand, or one CD28 ligand and some other foreign antigen, on the same, or different, tissue cells, can be mated to produce an animal that expresses both transgene products. The same effect can be achieved by introducing two separate transgenes into the same embryonal cell. In one embodiment, described in Example 2, a transgenic animal was produced containing transgenes encoding both B7 and a viral antigen, lymphocytic choriomeningitis viral (LCMV) glycoprotein (GP), in a form suitable for expression on pancreatic β cells. This transgenic animal, which also carry T cells specific for the LCMV GP and the appropriate MHC molecules, spontaneously develops insulinitis and diabetes.

Assays for CD28 Ligands

There are two classes of in vitro assays to determine whether a particular CD28 ligand is suitable for use in these methods: (1) assays that measure binding of the ligand to the extracellular domain of the CD28 receptor; and (2) assays that test for activation of the signal transduction pathways that are activated by the interaction of the CD28 receptor and an agonistic ligand. The first class of assays is useful to identify potential CD28 ligands, whereas the second class of assays is preferred to determine CD28 ligands that are suitable for use in the invention.

The first class of assays, which measure the binding of the potential ligand to the CD28 receptor, can be carried out by labeling, e.g., radioactively, a soluble CD28 receptor, e.g., a CD28-Ig fusion protein as described in Linsley et al., *J. Exp. Med.*, 173:721–730 (1991), which is incorporated herein by reference, and allowing this soluble receptor to bind with a potential CD28 ligand or a cell expressing the ligand. Bound ligands can be separated from non-binding ligands and detected by standard techniques and appropriate controls. Those ligands that bind to the CD28 receptor are potential CD28 ligands for use in the invention, and can be further tested by one of the assays described below.

The second class of assays, which determine CD28 receptor-mediated signal transduction, can be carried out in a number of ways. For example, a T cell proliferation assay is carried out in tissue culture dishes with purified T cells, which have been exposed to an antigen, or submitogenic amounts of phorbol 12-myristate 13-acetate (PMA) or immobilized antibodies to CD3, to provide the first stimulatory signal, and to cells modified to express a potential CD28 ligand. If a suitable CD28 ligand, such as a B7 polypeptide, is present on the modified cell, then the second, co-stimulatory signal will be delivered to the T cell, and the full effects of T cell activation will occur. As a control, in a second test, the T cells are first exposed to univalent (Fab) fragment of a CD28 monoclonal antibody, and then exposed to the potential CD28 ligand expressing cell. As described in Damle et al., *J. Immunol.*, 140:1753–61 (1988); and in Gross et al., *Nature*, 356:607 (1992), co-stimulatory activity through CD28 is not elicited by CD28 univalent (Fab) fragments. Therefore, costimulatory effects of, e.g., B7, are prevented under these conditions.

Another assay which can be used to determine CD28 receptor-mediated signal transduction is based on the recognition that T cell proliferation induced by CD28 ligands in combination with phorbol ester is entirely resistant to the effects of cyclosporine. June et al., *Mol. Cell. Biol.*, 7:4472 (1987), which is incorporated herein by reference. Cyclosporine resistance therefore can be used as a test for agonistic effects of potential CD28 ligands on the CD28 receptor. It is possible that other co-stimulatory receptors might have this property, but to date, it is believed that the effect is unique for CD28-mediated signal transduction.

A third assay method to determine CD28 receptor-mediated signal transduction can be carried out by screening for the effect of a potential CD28 ligand on tyrosine phosphorylation. Vandenberghe et al., *J. Exp. Med.*, 175:951 (1992), which is incorporated herein by reference, shows that the CD28 ligand B7 increases the tyrosine phosphorylation of a certain unknown 100 kDa substrate, and that this increase is prevented by pretreatment of the antigen-presenting cells that express B7 with an anti-B7 antibody. This same test can be carried out using a cell modified to express a potential CD28 ligand, and a corresponding antibody.

Assay for Expression of a CD28 Ligand

The transgenic animals and their non-transgenic littermates are sacrificed by cervical dislocation. RNA is then isolated from the pancreas, spleen, testis, lung, brain, kidney, thymus, liver, or other specific tissues as described in Chirgwin et al., *Biochem.*, 18:5294–5299 (1979), which is incorporated herein by reference. Using the technique of reverse transcriptase/polymerase chain reaction (RT/PCR), Chirgwin et al., supra, and Svetic et al., *J. Immunol.*, 147:2391–7 (1991), mRNA expression of a CD28 ligand, e.g., a B7 polypeptide, or other protein or growth factor (e.g., LCMV GP, TNFα) is assayed in the various tissues. By comparing the levels of the CD28 ligand mRNA in the various tissues of both the transgenic and nontransgenic animals, one can evaluate the ability of the transgene to direct expression of the ligand in a cell and tissue-specific manner.

This technique can also be used to distinguish between tissue cells in which the immature, unprocessed mRNA signal is present, and tissue cells in which correct splicing occurs to produce the final mRNA that is necessary for transgene expression.

Once tissue-specific expression of the ligand is demonstrated at the mRNA level, slices of specific tissue, e.g., pancreatic tissue, are obtained from a transgenic animal and a non-transgenic littermate and stained with anti-CD28 ligand antibody, such as the BB-1 monoclonal antibody (BB-1 mAb) directed against the human BB-1 molecule, Yokochi et al., *J. Immunol.*, 128:823–827 (1981), or an anti-murine B7 antibody, Reiser et al., *PNAS, USA*, 89:271–275 (1992), to demonstrate tissue-specific CD28 ligand expression. Other CD28 ligands, for which antibodies have not yet been prepared, are likely to be discovered and cloned. These ligands also fall within the scope of the present invention.

For example, one can demonstrate β cell-specific expression of B7 in mice carrying the insulin promoter-B7 constructs, acinar cell-specific expression of B7 in mice carrying the elastase promoter-B7 construct, or keratinocyte-specific expression with the K14 promoter construct.

Assays for Effects of Transgene Expression

Tissue samples can be assayed directly for histologic effects of the immune-mediated destruction of the cells expressing the CD28 ligand. Tissue slices of transgenic mice and non-transgenic but syngeneic mice are examined histologically for the presence of lymphocytic infiltration of the appropriate target tissue, which is considered to be the hallmark of T cell-mediated autoimmune diseases. See, e.g., Eisenbarth, *N. E. J. Med.*, 314:1360–1368 (1986); Wilson et al., *Ann. Rev. of Med.*, 41:497–508 (1990); and Lernmark et al., *Endocrinol. and Metabol. Clin. N. Amer.*, 20:589–617 (1991). Histological analysis of the appropriate tissues can be carried out at, e.g., 8 and 26 weeks of age. The infiltrate may be characterized by staining the tissue cells with CD4 and CD8 cell surface markers.

Assays of Therapeutic Agents to Treat Specific Autoimmune Diseases

One generally accepted symptom of the onset or progression of an autoimmune disease in animals is weight loss. Transgenic animals and non-transgenic but syngeneic animals are weighed weekly in the presence or absence (control) of a potential therapeutic agent for a particular autoimmune disease. Other symptoms characteristic of that autoimmune disease, such as blood or urine glucose levels in diabetes, or increased numbers of CD25 IL-2Rα$^+$ T cells or HLA DR$^+$ T cells in the blood circulation, are monitored once or more weekly. For example, urine can be regularly monitored for glycosuria, and blood factors may be measured using known diagnostic techniques. Symptoms of other autoimmune diseases include psoriatic skin lesions in psoriasis, weight loss and diarrhea in IBD, weight loss and pulmonary pathology in sarcoidosis, muscle weakness and paralysis in MS and TSP, bleeding and infection in aplastic anemia, and high or low levels of thyroid hormones in the blood and T cell infiltration of the thyroid gland in thyroiditis. These symptoms are well known to those of skill in treating these diseases.

The test results and disease symptoms in treated and untreated transgenic animals are then compared to determine the relative efficacy of the therapeutic agent in treating the particular autoimmune disease. An agent that effects an improvement in symptoms of greater than 20 percent, and preferably greater than 50 percent, e.g., a delay in the onset of the disease, prevention of weight loss or glycosuria, versus the control, is considered efficacious.

For a more detailed comparison, tissue slices from treated and untreated transgenic and non-transgenic animals are examined histologically for the presence of lymphocyte infiltration of the appropriate target tissue as described above. Comparison of tissues will allow the evaluation of the relative efficacy of the therapeutic agent in treating the particular autoimmune disease.

The potential therapeutic agents may be administered by various routes, including, e.g., by injection, e.g., intravenous, intraarterial, subcutaneous, intramuscular, or intradermal, by topical application, e.g., to an affected area of skin, or orally. For injection, the agents may be mixed with one or more pharmaceutically acceptable carriers, for example, saline or a physiologic buffer, which are known to those of skill in the art.

For topical administration, e.g., for psoriasis, a therapeutically effective amount of the agent is applied to the site of skin, or is combined with a pharmaceutically acceptable carrier, e.g., a spreadable cream, gel, lotion, or ointment, or a liquid such as saline. For use on the skin, the penetration of the agent into the diseased tissue may be accomplished by a variety of methods known to those of ordinary skill in this field.

For systemic administration, an effective amount of the agent is selected to achieve a certain concentration of the agent in the animal's blood. As is known in the medical field, the proper dosage to achieve this blood level of the agent may be determined by the animal's body weight. These dosages can be administered on a periodic basis, e.g., daily, weekly, or monthly, depending on clinical symptoms and the animal's response to treatment.

Another method of testing potential therapeutic agents involves an in vitro transgenic model, in which specific cells that express a CD28 ligand are removed from a transgenic animal and maintained or cultured in vitro. The therapeutic agent is then added to the cell culture, along with T cells from the animal, to determine whether the agent prevents destruction of the CD28 ligand expressing cells.

Models of Specific Autoimmune Diseases

The data presented in the Type I diabetes models below, support the general hypothesis that aberrant expression of the B7 ligand for the CD28 receptor on specific cells can, under appropriate conditions, result in diverse autoimmune diseases. Accordingly, models of specific autoimmune diseases can be generated using the methods and techniques described above, by making the modifications described below. In each case, a transgene operably linking a tissue-specific promoter with a specific animal's cDNA for a CD28 ligand, such as a B7 polypeptide, and any other DNA, such as introns, necessary for expression, is created using standard techniques.

The promoter-CD28 ligand transgene is then isolated from the plasmid backbone and injected into embryonal cells using standard techniques. Several examples of autoimmune diseases that can be mimicked using these techniques in a transgenic animal, such as a mouse, are enumerated below.

Psoriasis

A transgenic animal model of psoriasis can be made by producing an animal in which the keratinocytes express a CD28 ligand, such as a B7 polypeptide. Such an animal is created by introducing into an embryonal cell a transgene in which the expression of the CD28 ligand 1 is regulated by a keratin promoter, for example, the human keratin-14 (K14) promoter described in Cheng et al., *Genes Develop.*, 6:1444–56 (1992), which is incorporated herein by reference. This animal model can be used to assay inflammatory skin disease modulating agents.

Thyroiditis

A transgene which results in aberrant expression of a CD28 ligand on thyroid cells can be generated using a cDNA encoding the ligand operably linked to a bovine thyroglobulin gene promoter, such as the one described in Ledent et al., *EMBO J.*, 11:537–42 (1992), which is incorporated herein by references. These constructs can be used to produce a transgenic animal model of autoimmune thyroid disease. The efficacy of immunobiologic therapeutic agents directed against interaction of the ligand, aberrantly expressed on thyroid cells, with the CD28 receptor can then be studied in this animal model.

Sarcoidosis

A transgenic animal model of sarcoidosis, in which lung tissue cells express a CD28 ligand on their surfaces, can be created using a cDNA encoding the ligand operably linked to either a haptoglobin promoter, e.g., as described in D'Armiento et al., *Cell*, 71:955–961 (1992), or a human pulmonary surfactant protein gene promoter, e.g., as described in Wispe et al., *J. Biol. Chem.*, 267:23937–41 (1992), both of which are incorporated herein by reference. Such an animal model could be used to design and evaluate therapeutic agents to treat sarcoidosis.

Multiple Sclerosis and Tropical Spastic Paraparesis

It is likely that aberrant expression of B7 plays a role not only in MS, but also in TSP, as recent studies have shown that HTLV-1 infected T cells, which are associated with TSP, express B7 and CTLA-4. Freeman et al., *J. Immunol.*, 49:3795–3801 (1992). A transgenic animal model of MS and TSP, in which oligodendrocytes and/or Schwann cells express B7 polypeptides, can be created using a cDNA encoding a CD28 ligand operably linked to one of the myelin basic protein promoter/enhancer sequences described in Gow et al., *J. Cell. Biol.*, 119:605–16 (1992); and Foran et al., *J. Neurosci.*, 12:4890–7 (1992), which are both incorporated herein by reference. Such transgenic animals should be susceptible to immune-mediated demyelinating syndrome, and should provide a useful transgenic model for the evaluation of therapeutic agents for the treatment of MS and TSP in humans.

Inflammatory Bowel Disease

A transgenic animal model of Crohn's disease can be made by producing an animal in which small intestinal epithelium cells express a CD28 ligand, e.g., a B7 polypeptide. Such an animal is created with a cDNA encoding the ligand operably linked to one of the mouse or rat intestinal fatty acid-binding protein promoters described in Hauft et al., *J. Cell Biol.*, 117:825–39 (1992) and Roth et al., *PNAS USA*, 88:9407–11 (1991), which are both incorporated herein by reference. In addition, a transgenic animal model of ulcerative colitis can be made by designing a mouse to express a CD28 ligand on large bowel epithelial cells. Such a mouse can be created by using, for example, the rat glucagon promoter constructs of Lee et al., *J. Biol. Chem.*, 267:10705–8 (1992), which is incorporated herein by reference. Monitoring of these animals under different therapeutic regimes can provide useful data for the identification of compounds for the diagnosis, prevention, and therapy of these IBDs.

Aplastic Anemia

A transgenic animal model of aplastic anemia can be made by producing an animal in which the hematopoietic cells, such as stem cells, express a CD28 ligand, such as a B7 polypeptide. Such an animal is created by introducing into an embryonal cell a transgene in which the expression of the CD28 ligand is regulated by a CD34 promoter, for example, the human CD34 hematopoietic stem cell antigen promoter and 3' enhancer described in Burn et al., *Blood*, 80:3051–59 (1992), which is incorporated herein by reference. The cloning of the CD34 glycoprotein has been described in Simmons et al., *J. Immunol.*, 148:267–71 (1992). This animal model can be used to assay aplastic anemia modulating agents.

Assays for Therapeutic Agents for Treatment of Type I Diabetes

Generally accepted symptoms of the onset or progression of Type 1 diabetes in animals include glycosuria, hyperglycemia, and weight loss. Insulin promoter-B7 transgenic animals and non-transgenic but syngeneic animals are weighed weekly in the presence or absence of a potential therapeutic agent for diabetes. Urine sugars are monitored daily, and blood glucose is monitored once or more weekly via tail cuts. Blood glucose can be measured with Chemstrip bG II strips (Boehringer Mannheim, Indianapolis, Ind.), which require only one drop of blood per sample. The potential therapeutic agents, e.g., antibodies, peptides, or small molecules that block the interaction between the CD28 receptor and its ligands, can be administered by injection, e.g., intravenous, intraarterial, subcutaneous, or intramuscular, or by intradermal or oral application. For injection, the agents may be mixed with one or more pharmaceutically acceptable carriers, for example, saline or a physiologic buffer, which are known to those of skill in the art.

For systemic administration, an effective amount of the agent is selected to achieve a certain concentration of the agent in the animal's blood. As is known in the medical field, the proper dosage to achieve this blood level of the agent may be determined by the animal's body weight. These dosages can be administered on a periodic basis, e.g., daily, weekly, or monthly, depending on clinical symptoms and the animal's response to treatment.

The weight and urine or blood glucose levels in treated and untreated transgenic animals are then compared to determine the relative efficacy of the therapeutic agent in preventing or ameliorating Type 1 diabetes. An agent that effects an improvement in symptoms of 20 percent, and preferably 50 percent, e.g., a delay in the onset of the disease, or the prevention of weight loss, glycosuria, or hyperglycemia versus the control, is considered efficacious.

For a more detailed comparison, pancreatic tissue slices from treated and untreated transgenic and non-transgenic animals are examined histologically for the presence of lymphocyte infiltration, which is considered to be a reliable indication of Type I diabetes. See, e.g., Lernmark et al., *Endocrinol. Metabol. Clin. N. Amer.*, 20:589–617 (1991). Comparison of tissues will allow the evaluation of the relative efficacy of the therapeutic agent in treating the particular autoimmune disease.

EXAMPLE 1

Mouse Model of Type I Diabetes

A transgenic model of Type 1 diabetes can be made by producing an animal in which pancreatic β cells express the T-lymphocyte CD28 receptor stimulating ligand, B7. Transgenic mice expressing B7 on the surface of pancreatic β cells were created as follows.

A. Creation of RIP-B7-IpA Plasmid

Mouse B7 cDNA (described in Freeman et al., *J. Immunol.*, 143:2714–22 (1989); Freeman et al., *J. Exp. Med.*, 174:625–631 (1991)) was cleaved from its plasmid vector by cutting with the restriction enzyme Xba 1. A rat insulin 1 promoter plasmid (Soares et al., *Mol. Cell Biol.*, 5:2090–2103 (1985)), was cleaved at its 3' end with the restriction enzyme Hind III. The 5' overhanging regions of both the mouse B7 cDNA (1.5 kb) and the cleaved rat insulin 1 promoter plasmid were partially filled by standard techniques to allow for ligation of the two.

The resulting plasmid, RIP-B7, which contains the rat 1 insulin promoter operably linked with the mouse B7 cDNA, was then linearized by cutting with the restriction enzyme Hpa I, which cuts within the B7 cDNA downstream of the translation termination codon, but 5' of the endogenous polyadenylation signal. A 1.2 kb rat insulin 2 gene fragment (Accession Number J00748; LoMedico et al., *Cell*, 18:545–558 (1979)) was ligated into this Hpa I site to provide a 3' intron and polyadenylation site to create the plasmid pRIP-B7-IpA (pRIB-B7-IpA) shown in FIG. 1.

B. Creation of Transgenic Mice

The plasmid pRIB-B7-IpA was cut with restriction enzymes Sst I and Stu I and the resulting 3.0 kb gene fragment was purified by standard techniques. This transgene was injected into fertilized mouse oocytes from the strain Harlan FVB/N using standard techniques, e.g., as described in Leder et al., U.S. Pat. Nos. 4,736,866 and 5,175,383, which are incorporated herein by reference. The injected oocytes were re-implanted into pseudo-pregnant mice. Offspring were screened for the presence of the transgene and four founder mice were identified. These founder mice were individually tagged and used to establish transgenic mouse lines named for the founder's numbers 340, 353, 368, and 370.

C. Assay for Transgene Expression

The offspring of each founder were then assayed for B7 expression by staining pancreatic tissue sections using standard immunohistochemical techniques. Mice were anesthetized with methoxyfluorane. Left ventricles were cannulated and infused with saline to exsanguinate the animals prior to infusing 1% paraformaldehyde to fix the tissues. The pancreas of each was harvested and cut into 5 μm tissue sections for staining. Sections were incubated with 3 μg/ml hamster anti-mouse B7 antibody (provided by Repligen Corp., Cambridge, Mass.; described in Razi-Wolf et al. *Proc. Natl. Acad. Sci. USA*, 89:4210, 1992) for 30 minutes at room temperature. Alkaline phosphatase-labeled goat antibody to hamster immunoglobulins (Organon Teknika Corp., Durham, N.C.) was then applied for 30 minutes at room temperature. Alkaline phosphatase was detected using diaminobenzidine in $H_2O_2$ as a substrate. Offspring of two of the founders (378 and 340) revealed clear evidence of B7 expression.

Using the technique of Eastern analysis by reverse transcriptase-polymerase chain reaction (RT/PCR) as described in Golay et al., *PCR Methods and Appl.*, 1:144–145 (1991); and Svetic et al., *J. Immunol.*, 147:2391–7 (1991), founder mice where assayed for the tissue distribution of transgene expression. Mice were euthanized by $CO_2$ Asphyxiation, and RNA was isolated from several tissues of transgenic mice using standard guanidine isothiocyanate techniques as described, e.g., in Chirgwin et al., *Biochem.*, 18:5294–5299 (1979). To avoid cross-contamination, different disposable generators (OMNI Corp., Inc., Waterbury, Conn.) were used to homogenize each tissue during the RNA isolation procedure.

RNA from each tissue was gel equalized, then reverse transcribed to cDNA. Primers specific for transgene message-derived cDNA were employed to specifically simplify B7 mRNA transcribed by the transgene cDNA. The PCR primers, 5' (hybridizes to B7 cDNA) and 3' (hybridizes to distal region of the rat insulin 2 gene), were synthesized using standard techniques and had the following sequences:
5' TTT CAG CAC CGT GCT AGC (SEQ ID NO: 1)
3' ATG CTG GTG CAG CAC TGA (SEQ ID NO: 2)
The PCR products were first separated from each tissue by agarose gel electrophoresis and then transferred to nitrocellulose membranes. The membranes were then probed, using standard techniques, with an end-labeled oligonucleotide specific for the amplified transgene product. This probe was also part of the rat insulin 2 gene, and had the following sequence:
CGG TGA CCT TCA GAC CTT (SEQ ID NO: 3)
The probe oligonucleotide did not overlap with either PCR primer. RNA samples from transgene transfected and untransfected HIV-T15 cells (ATCC CRL 1777) were used as positive and negative assay controls.

In addition, PCR primers were employed that spanned the 500 bp intron of the rat insulin 2 gene to differentiate properly processed, mature mRNA from immature mRNA or contaminating genomic DNA. The PCR products amplified from genomic DNA or from unspliced mRNA were 835 base pairs in length, while those products amplified from properly spliced mRNA were 336 base pairs in length.

Figure 2:
FIG. 2 is a photograph of an Eastern blot of a reverse transcriptase-polymerase chain reaction (RT-PCR) assay demonstrating tissue-specific expression of B7 in a transgenic founder mouse from lines 378, 368, and 340, respectively.
Figure 2:
Figure 2:

As shown in FIG. 2, mice from line 378 exhibited efficient transgene mature mRNA expression only in the pancreas. This appears as a dark band on the gel in the bottom lane designated "336 bp," which represents the properly spliced mRNA, which has 336 base pairs. Low level transgene expression in the 336 bp lane was exhibited in the thymus, and ovary. The gel bands in the top lane designated "835 bp"

in the thymus, bone marrow, ovary, lung, and liver, and some in the pancreas, represent incompletely processed, immature mRNA that includes an intron which has not been properly spliced out. Transgene mRNA, whether or not processed, was not detected in brain, skeletal muscle, spleen, kidney, and heart. The partial expression of the mRNA in tissues other than the pancreas does not diminish the accuracy of this model for type 1 diabetes.

As shown in FIG. 2, mice from line 368 exhibited no transgene expression in the pancreas, and some detectable expression in the thymus, spleen, and liver. As shown in FIG. 2, mice from line 340 exhibited transgene expression in the pancreas, thymus, liver, kidney, and bone marrow.

Figure 3A:
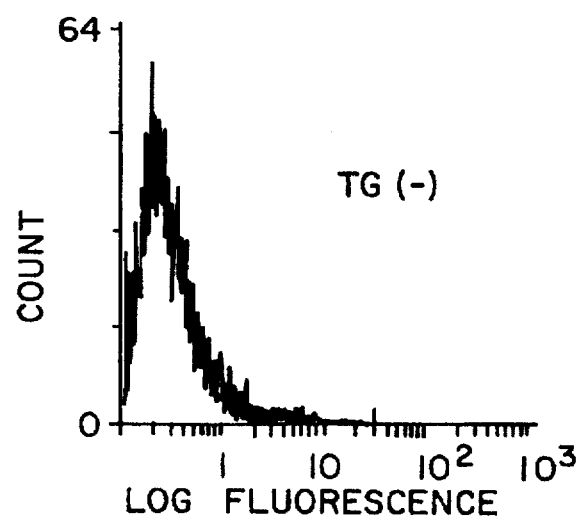
FIGS. 3A, 3B and 3C are graphic representations of cytofluorometric analysis of thymocytes from transgenic and nontransgenic but syngeneic control mice stained with biotinylated hamster anti-mouse B7 monoclonal antibody and incubated with streptavidin-PE.
Figure 3B:
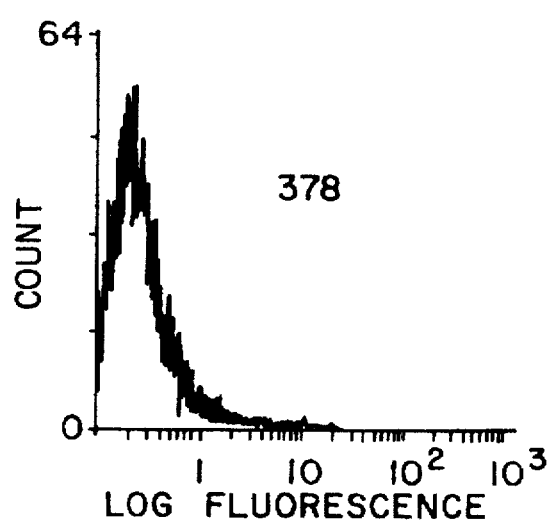
Figure 3C:
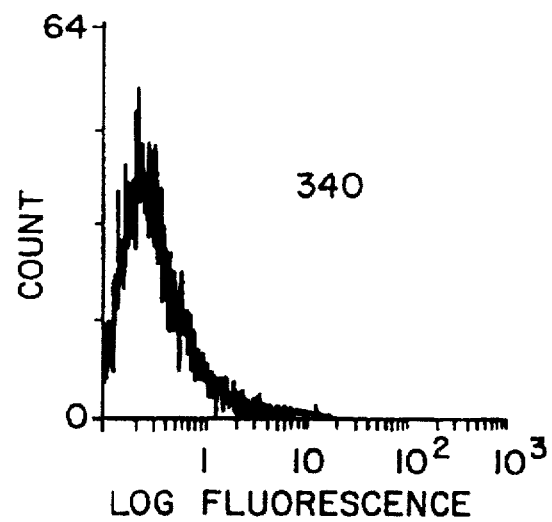
Figure 4A:
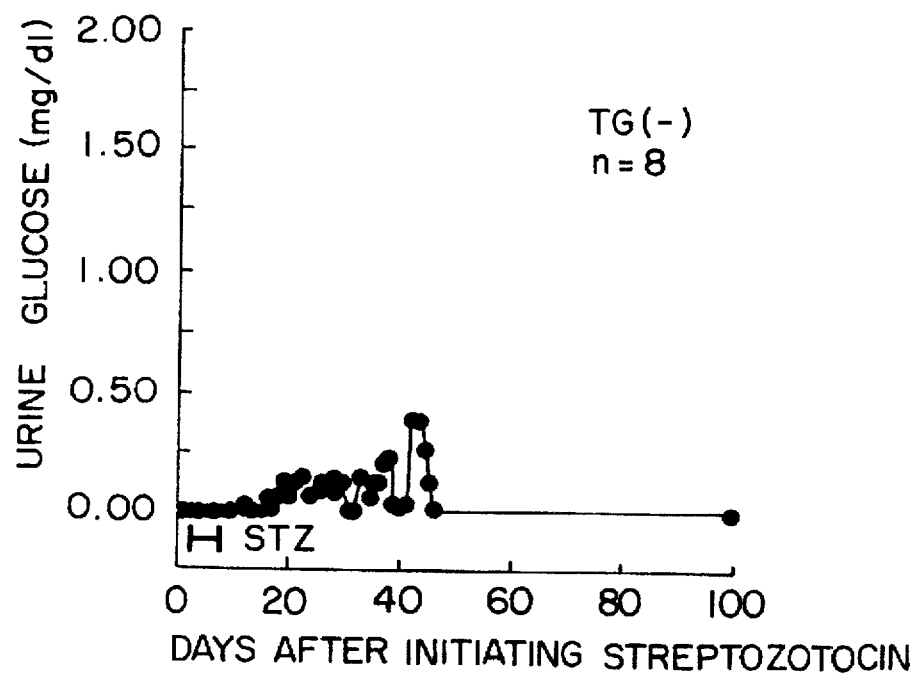
FIGS. 4A, 4B, 4C and 4D are graphic representations of streptozotocin susceptibility of founder line 378, 340, 368 and non-transgenic control mice.
Figure 4B:
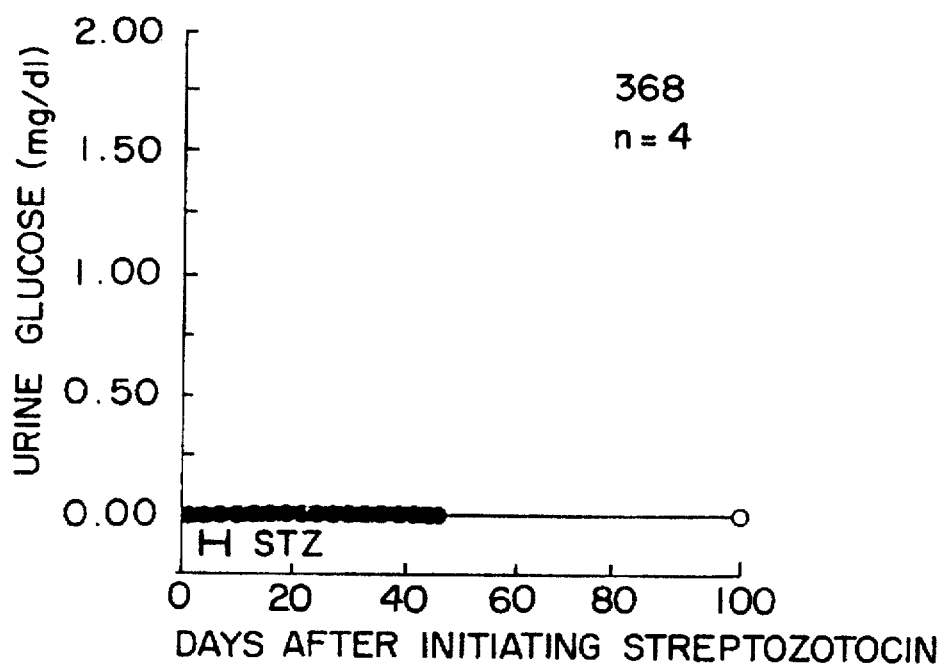
Figure 4C:
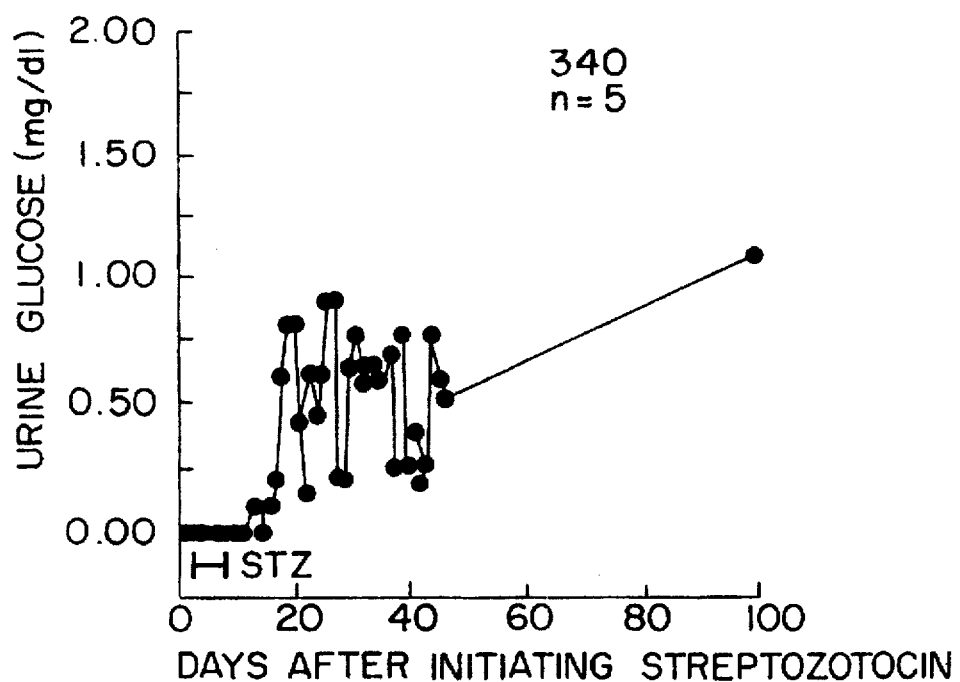
Figure 4D:
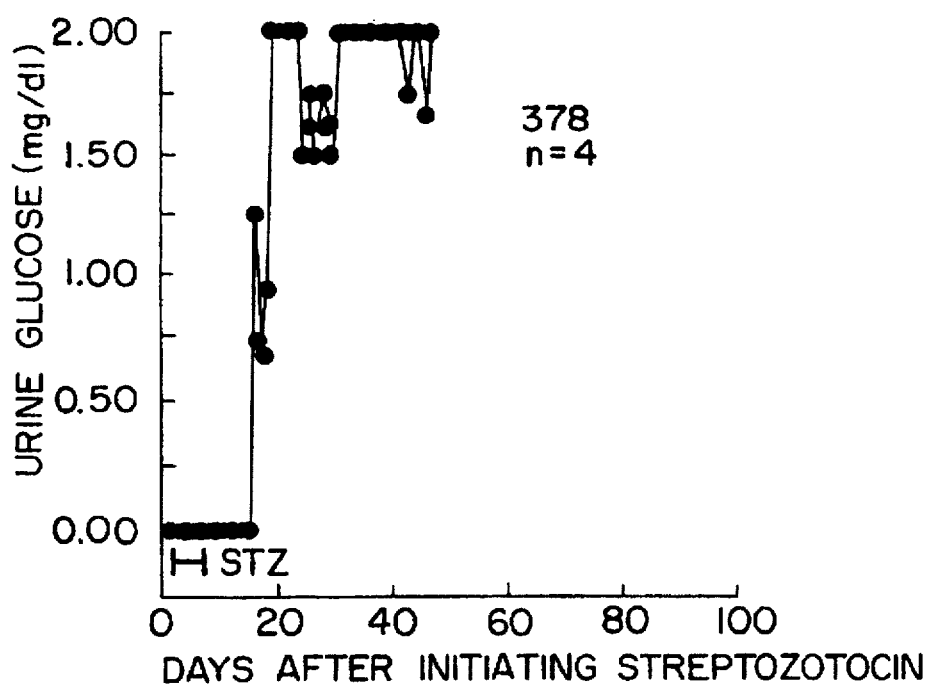

In order to correlate levels of transgene transcription in each of the mouse lines with B7 protein expression, immunohistochemical analysis on tissues taken from the mice was performed. Pancreatic sections harvested from the 340 and 378 line mice demonstrated islet staining with hamster anti-mouse B7 antibody, while the islets from the 368 line and non-transgenic mice did not stain. Transgene expression in tissues other than those predicted by a transgene's tissue specific promoter, especially if looked for using PCR, is well known to occur. For the B7 mice, the absence of Northern analysis evidence for bone marrow or thymic transgene expression suggests that either the level of transgene transcription in those tissues was small, or that a small subset of the cells from those tissues transcribed the transgene. Fluorescence activated cell sorting analysis, however, could not detect expression of the transgene product on thymocytes (FIG. 3) or on bone marrow cells. In this assay, thymocytes from mature mice were stained with biotinylated hamster anti-mouse B7 monoclonal antibody or control. The cells were then incubated with streptavidin-PE and the results displayed as logarithmic fluorescence intensity versus cell number. These data suggest that despite the RT-PCR evidence of transgene mRNA in the thymus and bone marrow, the transgene expression was one of low level and not of biological significance.

D. Functional Consequence of Transgene Expression

Transgenic mice were monitored for up to 24 weeks of age, with no indication of spontaneous onset of glycosuria, which would indicate diabetes. Therefore, the multi-dose streptozotocin model of insulin dependent diabetes mellitus (MDSDM) described in Rossini et al., *PNAS USA*, 74:2485–2489 (1977), which is incorporated herein by reference, was used to initiate diabetes in the transgenic mice. Previous reports have established MDSDM as a T cell-mediated autoimmune process, in that both insulitis and hyperglycemia can be prevented by T cell depletion, Herold et al., *Diabetes*, 36:796–801 (1987), or adoptively transferred with spleen cells, Kim et al., *Diabetes*, 33:771–777 (1984).

While STZ in high doses (70–250 mg/kg) induces diabetes through a direct beta cell toxic effect, multiple lower doses of the drug trigger an islet inflammatory response and, in certain mouse strains, an immunologically-mediated beta cell death (Rossini et al., 1977, Like and Rossini, 1976, Kolb and Kroncke, 1993). The mechanism of low-dose STZ-induced diabetes is complex but appears to be dependent upon up-regulated expression of beta cell antigens (Weide and Lacy, 1991, Herold et al., 1992) and the recruitment of lymphocytes (Wang et al., 1993). Transgenic and non-transgenic littermate mice were treated with multiple low-dose injections of STZ and the mice monitored with daily measurements of urine glucose for the onset of diabetes.

Streptozotocin 40 mg/kg/day (UpJohn Co., Kalamazoo, Mich.) in citrate buffer was injected into the peritoneum of four each of transgenic (line 378) and non-transgenic 6 to 7 week old Harlan FVB/N female mice on 5 successive days. Streptozotocin is not very stable once mixed with a buffer, so it is preferably administered within 10 minutes of preparation. Mice were then monitored for glycosuria (urine glucose level) to signal the onset of diabetes (Ames Keto-Diastix®, Miles, Inc., Elkart, Ind.). The results in FIGS. 4 and 5 show the mean urine glucose in mg/dl±the standard deviation for each day.

Within 15 or 16 days of the first streptozotocin injection, 4 of 4 from line 378 (FIG. 4), and 1 of 4 non-transgenic animals developed persistent glycosuria. The signs of persistent glycosuria in the one non-transgenic mouse remained low grade (1 mg/dl or less) and inconsistent. FIG. 4 shows the urine glucose level over 35 days in line 378 and non-transgenic mice. Streptozotocin was administered once daily on days 1 through 5, and the glucose level rose significantly on day 15 in the transgenic mice from line 378, indicating onset of diabetes, but showed only a small fluctuating increase in the nontransgenic littermates. In addition, on day 29, mean blood sugar in the transgenic mice was 581 mg/dl and 275 mg/dl in the non-transgenic mice.

FIG. 4 also shows the results of streptozotocin administration, as described above, in five transgenic mice from line 340 and in four non-transgenic littermates, respectively. Within 15 to 16 days of the first injection, 3 of 5 of the transgenic mice from founder line 340, and 0 of 4 of the non-transgenic mice developed glycosuria. FIG. 4 shows the results of streptozotocin administration in four transgenic mice from line 368, found to carry, but not express, the transgene in the pancreas cells. None of the four mice so treated developed glycosuria. The mice in FIG. 4 were monitored for 105 days, and had the streptozotocin administered for days 1 through 5. Syngeneic, but nontransgenic [TG (−)] did not develop glycosuria or had only transient or low level glycosuria.

One of the 340 line glycosuric animals was euthanized for histologic analysis, and showed a pancreatic islet mononuclear inflammatory infiltrate (islitis).

Figure 5A:
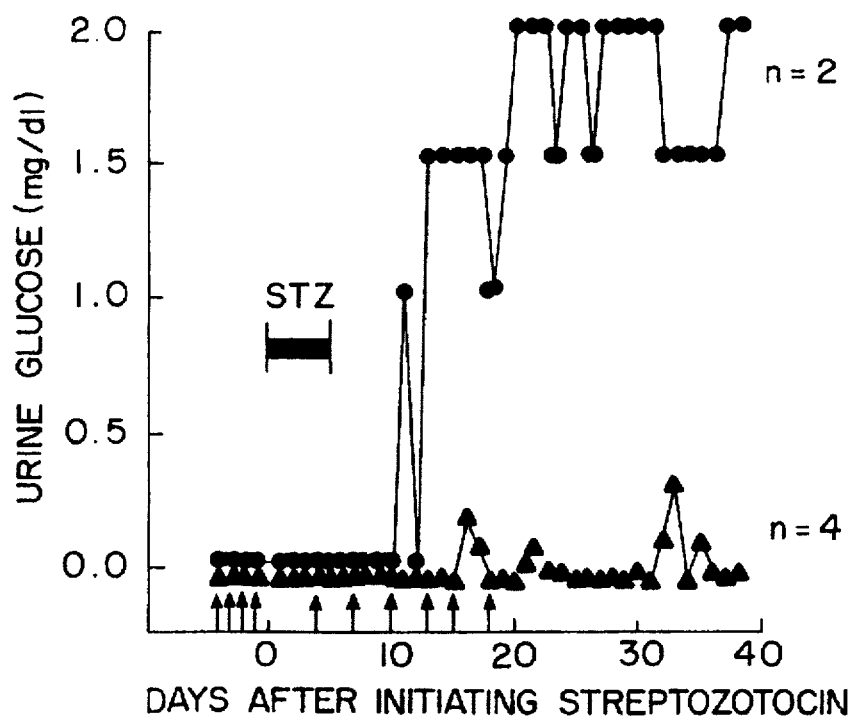
FIGS. 5A and 5B are graphic representations of the prevention of streptozotocin-induced diabetes in transgenic mice from the 378 line via administration of anti-CD4 and anti-CD8 antibodies or anti-B7 antibody.
Figure 5B:
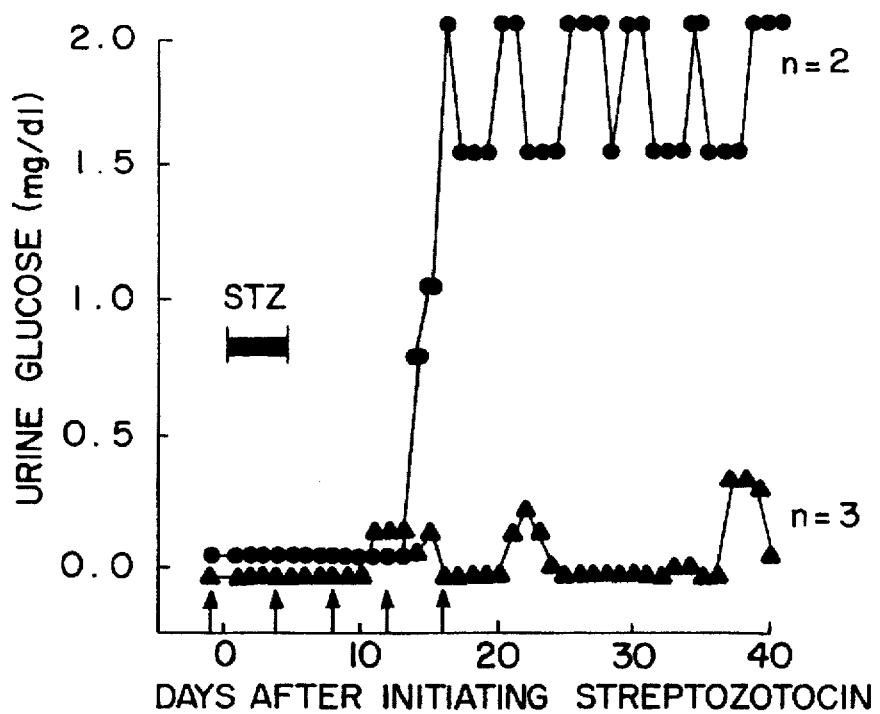

Other studies were performed to test whether multiple low-dose STZ-induced diabetes is mediated by T cells, and further whether the immune reaction is directed specifically against pancreatic beta cells. Mice from the 378 line, all heterozygous for the transgene, were given both anti-CD4 and anti-CD8 antibody prior to STZ treatment. The timing of antibody treatments is indicated by a (↑) in FIG. 5. The mean urine glucose is plotted on the y-axis. In FIG. 5A, B7 transgenic mice of the 378 founder line were treated with i.p. injections of PBS (●—●) or antibodies specific for mouse CD4 and CD8 (Δ—Δ) and observed for glycosuria after low dose streptozotocin. After receiving the first dose of streptozotocin (day 1) control animals developed persistent glycosuria on day 13, while antibody treated animals first developed low grade glycosuria on day 30–44. On day 29, mean blood glucose levels were 735 mg/dl for the control group and 281 mg/dl for the antibody treated group. In FIG. 5B, transgenic mice of the 378 founder line were treated with i.p. injections of PBS (●—●) or monoclonal antibody specific for mouse B7 (Δ—Δ). After receiving the first dose of streptozotocin (day 1) control animals developed persistent glycosuria on day 14, while antibody treated animals developed only sporadic glycosuria. On day 22, mean blood glucose levels were 629 mg/dl for the control group and 249 mg/dl for the antibody treated group.

These results demonstrate that administration of these anti-T cell antibodies prevented diabetes onset (FIG. 5A). Anti-mouse B7 monoclonal antibody treatment also prevented diabetes following STZ treatment in the transgenic mice (FIG. 5B). Immunohistologic analysis of transgenic mice treated with multiple low-dose STZ revealed insulitis and periinsulitis with infiltrates containing both $CD4^+$ and $CD8^+$ T cells. Finally, pancreatic tissue sections from a 378 line mouse, treated with multiple low-dose STZ to induce diabetes, were also analyzed for glucagon and insulin containing cells. While immunohistologic analysis revealed glucagon staining (alpha) cells in islet remnants, very few insulin staining (beta) cells were seen. Together these data demonstrate that the enhanced STZ susceptibility of the B7 transgenic mice is secondary to T lymphocyte mediated, beta specific killing. Further that B7 is a required component in the pathway resulting in the beta cell killing.

EXAMPLE 2

A Triple Transgenic Mouse As a Type I Diabetes Model

The triple transgenic mouse expressing both B7 and the lymphocytic choriomeningitis virus (LCMV) glycoprotein (GP) on pancreatic beta cells, and a transgenic T cell receptor (TCR) specific for LCMV GP peptide 33–41 in the context of $H-2D^b$ (Ohashi et al., Cell, 65:305–317 (1993)) was produced. This transgenic mouse spontaneously developed pancreatic islet lymphocytic infiltrate (insulitis) and diabetes.

METHODS AND MATERIALS

Breeding: To produce triple transgenic mice, the 378 line B7 transgenic mice ($H-2^q$) were crossed with mice ($H-2^b$) transgenic for either or both the LCMV GP or TCR transgenes. The cross resulted in some mice expressing both LCMV GP and mouse B7 on pancreatic beta cells (B7-GP double transgenics, $H-2^{bxq}$), and other mice expressing B7 on their beta cells and the transgenic TCR on their T lymphocytes (B7-TCR double transgenics, $H-2^{bxq}$). With further breeding mice were obtained that carried all three transgenes, i.e., the LCMV GP-B7-TCR triple transgenic mice. In all cases, the pair bred to create the triple transgenic mice included one member homozygous for $H-2^b$ to insure that the offspring would carry the $H-2^b$ haplotype necessary for LCMV-GP presentation to the transgenic TCR T cells. The three following breeding pairs were employed: GP-TCR ($H-2^b$)×B7 ($H-2^q$); B7-GP ($H-2^{bxq}$)×TCR ($H-2^b$); and B7-TCR ($H-2^{bxq}$)×GP-TCR ($H-2^b$).

Typing of transgenic animals: DNA was isolated from tail biopsies utilizing proteinase K methods previously described (Hogan et al., *Manipulation of the Mouse Embryo: A Laboratory Manual* (Cold Spring Harbor Laboratory Press), (1986); Ohashi et al., *J. Immunol.*, 150:5185–5194). In some cases the B7 transgene was detected by standard genomic Southern technique: the DNA was cut with EcoRI, subjected to gel electrophoresis, transferred to Nytran (Schleicher and Schuell, Keene, N.H.), then probed with a 722 bp PstI fragment of the Rat 1 insulin promoter-B7 DNA construct. The transgenes for LCMV GP, the TCR α-chain, and in some cases B7 were detected by polymerase chain reaction. The primer pairs used were:

LCMV GP: 5'-CAAGCAAGATGTAGAGTCTGCG (SEQ ID NO:4);

and 5'-GGCTTTGGACATGAACCGCCC (SEQ ID NO:5);

TCR α-chain: 5'-CGAGGATCCTTTAACTGGTA CACAGCAGG (SEQ ID NO:6);

and 5'-CTGACCTGCAGTTATGAGGACAGCAC (SEQ ID NO:7);

B7: 5'-CAAACAACAGCCTTACCTTCGG (SEQ ID NO:8);

and 5'-GCCTCCAAAACCTACACATCCT (SEQ ID NO:9).

Immunohistochemistry: For peptide hormones staining, pancreata were fixed in 10% formalin and embedded in paraffin. Sections were then cut, treated with trypsin for 15 minutes (for insulin staining), and stained the insulin-specific Mab 3 monoclonal antibody (Storch et al., *Diabetes*, 34:808–811 (1985)) at a 1:30,000 dilution. Using the protein A-gold technique (Roth et al., *Virchows Arch. B. Cell Pathol.*, 63:51–61 (1992)), a color reaction was developed. Adjacent tissue sections were stained with hematoxylin and eosin. For cell surface receptor staining, pancreata were snap frozen in liquid nitrogen and 5 µm thick cryostat sections were cut and fixed in acetone for 10 minutes. These sections were then incubated with the primary antibodies YTS169.4.2 (anti-CD8) (Cobbold et al., *Nature*, 312:548–551 (1984)), YTS191.1 (anti-CD4)(Cobbold et al., *Nature*, 312:548–551 (1984)), F4/80 (anti-macrophage) (Austyn et al., *Eur. J. Immunol.*, 11:805–815 (1981)), anti-B220, or biotinylated hamster anti-mouse B7 (Razi-Wolf et al., *Proc. Natl. Acad. Sci. U.S.A.*, 89:4210–4214 (1992)) (obtained from the Repligen Corporation, Cambridge, Mass.). For B7 staining, sections were pre-incubated with 1% bovine serum albumin then washed with phosphate buffered saline (PBS) prior to the 60 minute, room temperature reaction with the anti-B7 antibody. The sections were then treated with Extravidin-HRP (Sigma, St. Louis, Mo.) for 60 minutes, and the color was developed by incubating with 0.1% diaminobenzidene (DAB)/0.03% $H_2O_2$ for 15 to 20 minutes. For other than B7 surface staining, the primary antibodies were followed by a two-step indirect immunoenzymatic staining procedure. Goat anti-rat Ig (TAGO, Burlingame, Calif.) labeled with alkaline phosphatase was added for 30 minutes at room temperature and then alkaline phosphatase-labeled anti-goat antibodies (Jackson Immunoresearch, PA) were added for another 30 minutes. Antibody dilutions were prepared in 0.1M Tris-HCl (pH 7.4) containing 5% normal mouse serum. Alkaline phosphatase was then detected by a red color reaction, by using naphthol A-BI phosphate and New Fuchsin. Endogenous alkaline phosphatase was blocked with levamisol. Some sections were then counterstained with Mayer's hemalum for 2 minutes.

Quantitation of Glucose in the Urine and Blood: The glucose level in urine samples was measured using Keto-Diastix® (Miles Inc., Elkhart, Ind.), and blood glucose measurements were determined using the HemoCue test kit (Angelholm, Sweden).

Cytotoxicity Assay: EL-4 ($H-2^b$) cells were selected as targets for the cytotoxic T cell (CTL) assay: some were pulsed with the p33–41 peptide of LCMV GP, while others were not pulsed. These cells were then labeled with $^{51}$chromium for 2 hr. Target cells were then washed three times and counted. Approximately $1×10^4$ target cells were plated in 96 well round-bottomed plates with spleen effector T cells. Effector T cells were activated in vitro for three days with LCMV-infected and irradiated macrophages in the absence of exogenous IL-2. The cells were then incubated in vitro at various effector:target ratios but always in a final volume of 200 µl. After a 4–5 hr incubation at 37° C., 70 µl of the supernatant was removed and counted. Percent specific release was calculated as previously described (Pircher et al., *Eur. J. Immunol.*, 17:159–166 (1987)). Spontaneous release of $^{51}$chromium from targets was less than 20%.

RESULTS AND DISCUSSION

A. Diabetes Onset in Triple Transgenic Mice

Two founder mice exhibited B7 expression on the beta cells. The 378 line revealed the most intense beta-cell B7 immunostaining so that line was studied in detail. Expression of the B7 transgene in other tissues was examined by immunostaining and by Northern analysis: no expression was evident. Approximately 100 B7 mice hemizygous (+/−) for the transgene were followed, several for up to one year, for the development of glycosuria. No spontaneous diabetes was observed and histologic examination of pancreata revealed that islet architecture remained normal.

To test the influence of pancreatic beta cell B7 expression on the potentially self-reactive but unresponsive $CD8^+$ transgenic T cells in the previously described LCMV GP-TCR mice (Ohashi et al., Cell, 65:305–317 (1991)), LCMV GP-TCR mice were crossed with B7 transgenic mice. In striking contrast, all of the B7-LCMV GP-TCR triple transgenic (14/14) spontaneously developed diabetes. The median age of the triple transgenic mice at time of hyperglycemia onset was 9–10 weeks, with one mouse developing diabetes at 7 weeks of age, and one as late as 14 weeks. None of the LCMV GP-TCR, B7-TCR, or B7-LCMV GP double transgenic mice, followed for up to 11 months, became diabetic (Table I).

TABLE I

Onset of Diabetes in B7-LCMV GP, B7-TCR, and LCMV GP-TCR Double and LCMV GP-B7-TCR Triple Transgenic Mice

| Transgenic Mouse Line | Animal Number | Proportion with Diabetes | Age |
|---|---|---|---|
| B7-GP | 27 | 0/27 | 4 weeks–11 months |
| B7-TCR | 36 | 0/36 | 4 weeks–11 months |
| GP-TCR | 24 | 0/24 | 4 weeks–11 months |
| GP-B7-TCR | 14 | 14/14 | 7–14 weeks at onset of hyperglycemia |

B. Histologic Analysis of Pancreas Sections

Figure 6A:
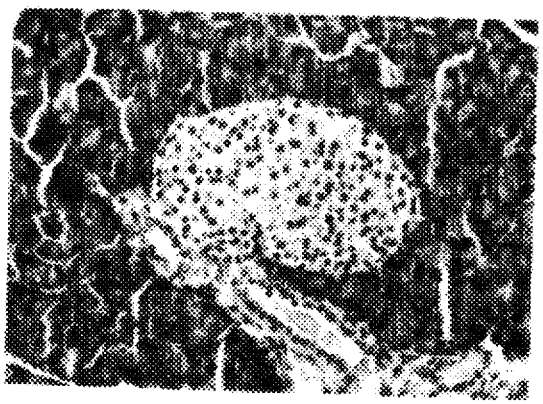
FIGS. 6A–6H are photographs of histologic analysis of pancreas sections stained with hematoxylin and eosin (left) or anti-insulin antibodies (right). Panels A and B: LCMV GP-TCR animals; Panels C and D: B7-GP animals; Panels E and F: B7-LCMV GP-TCR (pre-diabetic) animals; and Panels G and H: B7-LCMV GP-TCR (diabetic) animals.
Figure 6B:
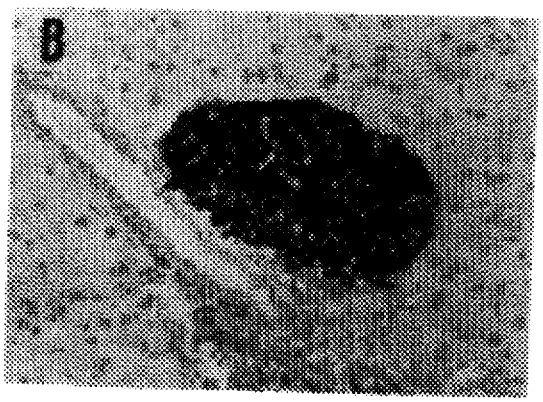
Figure 6C:
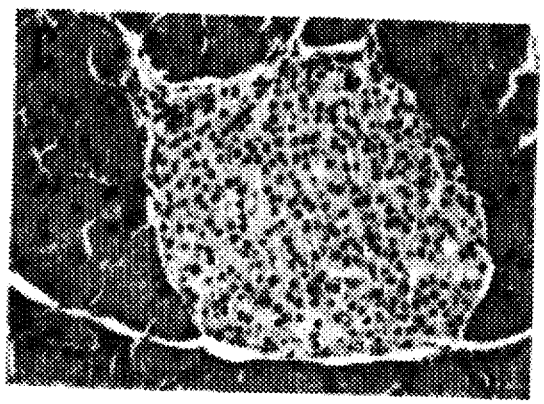
Figure 6D:
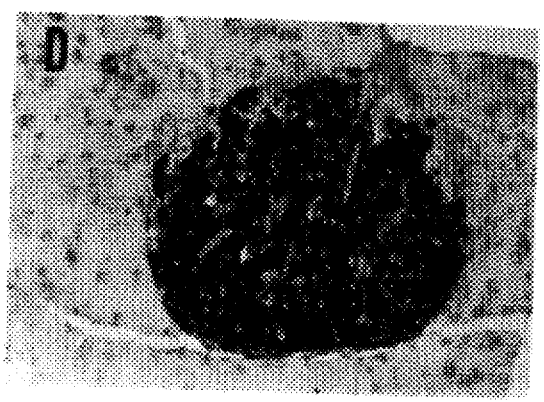
Figure 6E:
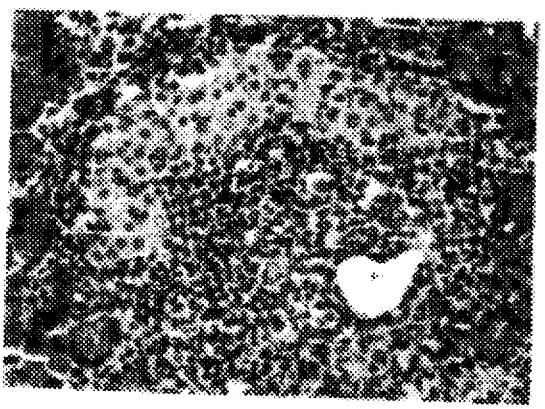
Figure 6F:
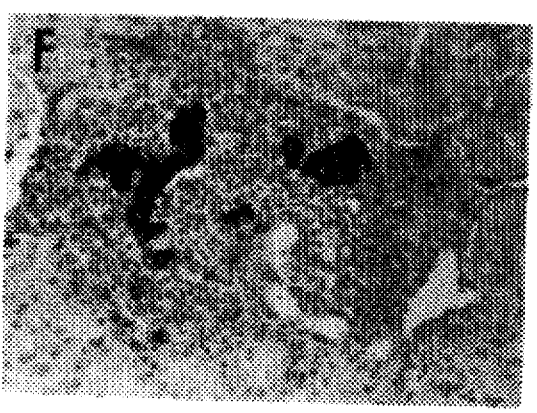
Figure 6G:
Figure 6H:
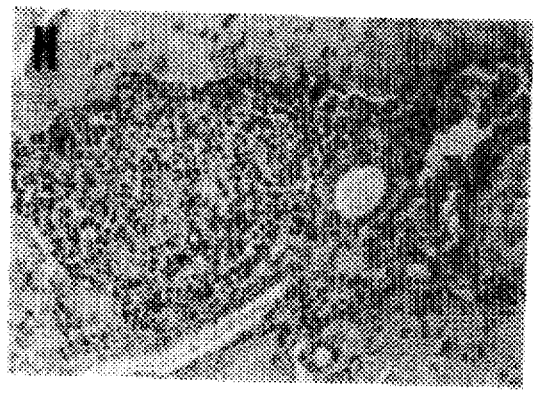

To further analyze the functional properties of pancreata from the different transgenic mice, histologic analysis was performed. In FIG. 6, photos are all paired, the left sided sections were stained with hematoxylin and eosin and the adjacent sections, shown on the right, were stained with anti-insulin antibodies. Sections from LCMV GP-TCR animals (A and B) and from B7-LCMV GP animals (C and D) reveal normal islet architecture, no lymphocytic infiltrate, and normal immunostaining for insulin. On the other hand, pancreatic sections from a 10 week old, not yet diabetic LCMV GP-B7-TCR mouse revealed an ongoing insulitis with a diminished but still present mass of beta cells (FIG. 6E and F). Moreover, pancreatic sections taken from a 10 week old, diabetic triple transgenic mouse and stained with anti-insulin or anti-glucagon antibodies revealed the presence of alpha cells in the islet cell remnants, but the total absence of insulin-producing beta cells (FIG. 6H). The onset of hyperglycemia in the triple transgenic mice was followed by ketosis, wasting, and ultimately a fatal outcome consistent with the histologic evidence for complete beta cell destruction.

C. Analysis of Islet Infiltrating Cell Phenotype

To examine the phenotype of the islet infiltrating cells, pancreatic sections from a 9 week old euglycemic LCMV GP-TCR mouse and from two triple transgenic mice, one 4 weeks old and not yet diabetic and one 9 weeks old and diabetic, were subjected to additional immunohistologic analysis (FIG. 7). The sections were stained with monoclonal antibodies specific for CD8 (A–C), CD4 (D–F), macrophages (G–I), or B lymphocytes (J–L). Pancreas frozen sections were incubated with the primary antibodies YTS169.4.2 (anti-CD8) (Cobbold et al., Nature, 312:548–551 (1984)), YTS191.1 (anti-CD 4)(Cobbold et al., Nature, 312:548–551 (1984)), F4/80 (anti-macrophage) (Austyn et al., Eur. J. Immunol., 11:805–815 (1981)), or anti-B220. The primary antibodies were followed by a two-step indirect immunoenzymatic staining procedure. Sections were counterstained with Mayer's hemalum for 2 minutes.

These studies revealed few, if any, immune cells in the pancreas of the LCMV GP-TCR mouse (FIG. 7A, D, G, and J). Alternatively, the sections from the 4 week old LCMV GP-B7-TCR mouse demonstrated a mixture of a few, faintly stained $CD8^+$ and $CD4^+$ T lymphocytes (FIGS. 7B and E respectively) and an increased number of macrophages (FIG. 7H) surrounding the pancreatic islets. Sections taken from the diabetic triple transgenic mouse revealed a severe insulitis and peri-insulitis with $CD8^+$ and $CD4^+$ T lymphocytes, macrophages (FIGS. 7C, F, and I respectively), and B lymphocytes (FIG. 7L) infiltrating the islets.

D. Response of Transgenic Mice to Infection with GP Expressing Recombinant Vaccinia To further evaluate the absence of spontaneous diabetes in double and single transgenic mice, their response to infection with a recombinant vaccinia virus expressing LCMV GP (vacc-gp) was studied. Interestingly, all four of the B7-LCMV GP double transgenic mice infected with $2 \times 10^6$ p.f.u. of vacc-gp developed diabetes 6 to 10 days after infection. Three B7 and 15 LCMV GP single transgenic and 2 B7-TCR double transgenic mice were similarly infected with vacc-gp; none developed diabetes however pancreatic sections from the infected LCMV GP mice did reveal a mild insulitis as previously reported (Ohashi et al., J. Immunol., 150:5185–5194 (1993)). The present result suggests that the susceptibility of B7-LCMV GP mice to vacc-gp induced diabetes is due to beta cell B7 expression supporting a self-perpetuating destructive autoimmune process. Since vacc-gp infection did not lead to diabetes in the LCMV GP, B7, or B7-TCR mice, the response was not a non-specific sequela of the viral infection. These vacc-gp infection data also indicate that LCMV GP-specific T lymphocytes are not clonally deleted in the B7-LCMV GP mice. The observation that B7-LCMV GP mice never spontaneously develop diabetes suggests the importance of the antigen-specific T cell precursor frequency in this model.

D. Lymphocyte TCR and Functional Assays

Figure 8:
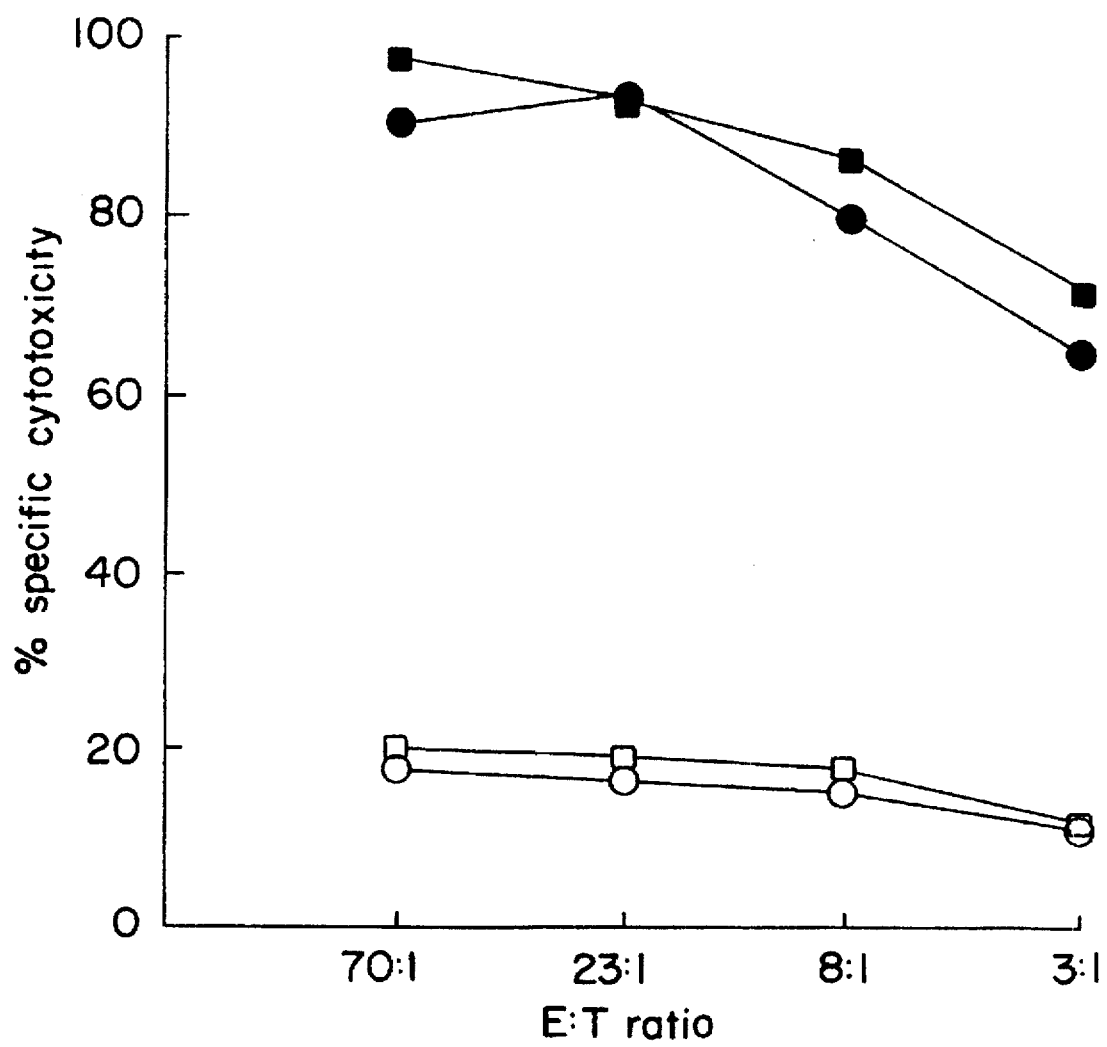
FIG. 8 is a graphic representation of the effector function of splenic cells from LCMV GP-TCR double (squares) and LCMV GP-B7-TCR triple (circles) transgenic mice in a cytotoxicity assay. Target cells pulsed with the peptide (closed symbols) were efficiently lysed while cells not pulsed with peptide (open symbols) were not.

In view of the disparate outcomes observed in the LCMV GP-TCR double transgenic and the LCMV GP-B7-TCR triple transgenic mice, studies to determine their T lymphocyte cell surface receptor and functional status were performed. For both the LCMV GP-TCR double and the LCMV GP-B7-TCR triple transgenic mice, approximately 80% of $CD8^+$ lymph node T lymphocytes stained with antibodies specific for the transgenic TCR. These data are consistent with similar analysis previously reported for the LCMV GP-TCR double transgenic mice (Ohashi et al., Cell, 65:305–317 (1991)) and reflect the skewing of the T cell repertoire toward $CD8^+$ cells driven by the positive selection of T cells expressing the transgenic TCR. The functional capacity of the T lymphocytes from the double and triple transgenic mice was measured in a cytotoxicity assay. In FIG. 8, the effector function of splenic cells from LCMV GP-TCR double (squares) and LCMV GP-B7-TCR triple (circles) transgenic mice was compared in a cytotoxicity assay. Target cells pulsed with the peptide (closed symbols) were efficiently lysed while cells not pulsed with peptide (open symbols) were not. Data from three different triple transgenic mice, and from one double transgenic mouse are represented. The splenic effector cells for these studies were tested after 3 days of in vitro activation.

As shown in FIG. 8, CTLs derived from the double and triple transgenic mice were equally able to lyse target cells presenting the appropriate LCMV GP epitope. This demonstrates that the self-reactive T cells could be activated in vitro and therefore are not impaired in their effector function. Thus, no evidence for T cell anergy was detected to explain the absence of pancreatic beta cell killing in the LCMV GP-TCR mice (Ohashi et al., Cell, 65:305–317 (1991)). These results suggest that self-reactive T cells in LCMV GP-TCR mice are not activated because the pancreatic beta cells do not deliver a costimulatory signal.

CONCLUSION

Previously reported studies of double transgenic mice (called LCMV GP-TCR) that express both the LCMV glycoprotein (GP) on pancreatic beta cells and the TCR specific for the LCMV-GP in the context of H-2D$^b$, demonstrated the surprising result that antigen-specific T lymphocytes in the context of appropriately presented antigen could coexist in the same animal without immunologic sequela (Ohashi et al., Cell, 65:305–317 (1991). These LCMV GP-TCR double transgenic mice rapidly developed diabetes, however, once infected with LCMV. Together these results suggested that once activated, the transgenic T cells were fully capable of normal effector function against appropriate targets and further suggested that pancreatic beta cells were either shielded from and/or were incapable of activating the transgenic T cells.

As described herein, by breeding the B7 transgenic mouse with the previously reported TCR-LCMVGP double transgenic mouse (Ohashi et al., supra 1991) the LCMVGP-B7-TCR triple transgenic mouse was created. These triple transgenic mice spontaneously develop type I diabetes. Moreover, the triple transgenic mice recapitulate in vivo the components felt to be necessary to activate T cells in vitro. These results demonstrate that B7 expression on other than professional antigen presenting cells can contribute to a breakdown in immune tolerance toward those cells in vivo.

Neither the B7 transgenic nor any of the double transgenic mice created for these studies (i.e. LCMV GP-TCR, B7-LCMV GP, and B7-TCR double transgenic mice) spontaneously developed diabetes or insulitis. Studies were performed to explore the possibility that the tolerance observed was secondary to β-cell specific T cell clonal deletion. The presence in the thymus of a B7 transgene mRNA derived signal further raised our concern that thymic T cell selection may have been influenced in the B7 transgenic mice. To explore the consequence of thymic B7 transgene mRNA expression, thymocytes from the transgenic an non-transgenic littermate mice were stained for B7 and no differences in cell surface expression were observed. Moreover, the availability of reagents to specifically label the T lymphocytes expressing the transgenic TCR allowed quantitation of the these T cells' contribution to an animal's lymphocyte repertoire. In the B7-TCR and LCMV GP-TCR mice, the transgenic T cells predominated the lymphocyte repertoire, accounting for 60–80% of the circulating CD3$^+$ cells. Thus, in none of the double transgenic mice expressing the transgenic TCR was T cell clonal deletion responsible for the tolerance observed. For the B7-LCMV GP double transgenic mice, the existence of LCMV GP antigen specific T cells was inferred from the observation that vacc-gp infection induced insulitis and diabetes. Thus, clonal deletion does not explain the tolerance observed in these mice. In addition, while a transgene encoded B7 mRNA signal can be detected in the thymus by RT-PCR, B7 is not overexpressed on thymocytes from these mice. It is possible that the B7 transgene resulted in the expression of B6 on thymic cells other than the thymocytes were examined. If so, that B7 expression did not measurably affect the T cell repertoire. B7 is known to be expressed by thymic epithelial cells (Turka et al., J. Immunol., 146:1428–1436 (1991).

In another transgenic mouse model, it has been shown that down-regulation of T cell receptors on self-reactive T cells can result in tolerance in vivo (Schönrich et al., Cell, 65:293–304 (1991). When T lymphocytes from triple, double (LCMVGP-TCR, B7-TCR), or TCR transgenic mice were stained using clonotype specific antibodies however, no difference in the staining intensity of their CD8$^+$ T cells was detected.

Others have demonstrated the natural existence of potentially autoreactive islet cell specific T lymphocytes in vivo (Burtles et al., J. Immunol., 149:2185–2193 (1992). Obviously, these lymphocytes do not normally initiate beta cell destruction however. The uneventful coexistence of antigen specific T cells with potential targets has generally been attributed to one of three mechanisms occurring alone or in combination: T cell clonal anergy, T cell suppression, and/or the broad category of immune ignorance. Each of these tolerance mechanisms is mediated by a different cell type. In clonal anergy, the T cells are themselves functionally inactivated. In immune ignorance, the cells presenting the antigen are either shielded from autoreactive T cells, or they insufficiently trigger the T cells. The third tolerance mechanism requires the intervention of a third cell type, i.e. the suppressor cell.

One approach to understanding T lymphocyte tolerance has been to study the immunologic abnormalities occurring in autoimmune states, i.e., when tolerance mechanisms fail. Three general autoimmunity mechanisms have been proposed (Roitt, Essential Immunology (Oxford, England: Blackwell Scientific Publications), 315–324 (1991). One, a tolerance bypass mechanism whereby an abnormal self-antigen or a cross-reacting antigen results in activation of a T cell clone with self reactivity. Two, a breakdown of normal suppressor mechanisms; either a loss of cells subserving the suppressor function, or a defect in which cells normally unable to present antigens to helper T cells, gain that function. Indeed, the upregulated cellular expression of MHC class II molecules observed in several autoimmune states (type I diabetes, Graves' disease) has been studied in several transgenic models (Lo et al., Cell, 53:159–168 (1988); Böhme et al., Science, 244:1179–1183 (1989); Markmann et al., Nature, 366:476–479 (1988); Miller et al., J. Immunol., 144:334–341 (1990). Three, an immune imbalance induced by cytokine dysregulation which may in turn lead to upregulated expression of MHC molecules or adhesion molecules, or may even convert previously anergic cells into antigen responsive cells. In fact, to date only three transgenic mouse models have resulted in both insulitis and diabetes (Sarvetnick et al., Cell, 52:773–782 (1988); Stewart et al., Science, 260:1942–1946 (1993); Heath et al., Nature, 359:547–549 (1992); transgenic mice with islets that constitutively express interferon-α or interferon-γ, and triple transgenic mice with transgenic T cells with K$^b$ specificity and whose beta cells express both the class I molecule H-2K$^b$ and interleukin-2.

Using the general classification of autoimmune mechanisms discussed above (Roitt, supra (1991), the dysregulated expression of a B7-like molecule would be categorized as a breakdown of a normal suppressor mechanism. That is, β cells which are normally unable to present antigens in such a way so as to activate an immune response, gain that function. Three different lines of evidence presented herein support the conclusion that pancreatic β cell B7 expression lowers the threshold for the activation of β cell antigen-specific T lymphocytes. One, the B7 transgenic mice compared with syngeneic, non-transgenic littermates demonstrated increased susceptibility to multiple low-dose STZ, a well described model for type I diabetes (Rossini et al., Proc. Natl. Acad. Sci. USA, 74:2485-2489 (1977), Like et al., Science, 193:415-417 (1976); Kolb et al., Diabetes Rev., 1:116-126 (1993). That this differential susceptibility was secondary to immune system activation was demonstrated by the ability of α-CD4 and α-CD8 antibody injections to block STZ induced diabetes. Two, B7-GP mice compared with GP transgenic mice displayed differential susceptibility to diabetes resulting from vacc-gp infection. Three, while none of 24 LCMV GP-TCR double transgenic mice observed for this study developed diabetes spontaneously, 11 of 16 triple transgenic mice developed diabetes by 14 weeks of age (Table I).

Thus, the dysregulated expression of costimulatory molecules like B7 is now shown to be another potential mechanism underlying autoimmune disease. As is the case for transgenic mice expressing interferon-α or interferon-γ in beta cells, some insult (e.g. viral infection) may induce epithelial cells to express B7, or B7-like molecules. Indeed it has recently been reported that thyroid biopsies from patients with autoimmune Graves' thyroiditis reveal thyroid-cell specific anti-B7 immunostaining (García-C ózar et al., Immunologia, 12:32 (abstract 98) (1993). Thyroid cells from normal individuals did not stain, but B7 immunostaining could be induced by incubating the normal thyroid cells in 8-bromo-cAMP (García-Cozar et al., Immunologia, 12:32 (abstract 98) (1993). In addition, others have found that psoriatic but not unaffected skin keratinocytes stain with the BB-1 antibody which stains a B7-like molecule and that the intensity of the immunostaining could be increased by incubating the cells in vitro with interferon-γ plus 12-o-tetradecanoyl phorbol 13-acetate ester (TPA) (Nickoloff et al., Am. J. Path., 142:1029-1040 (1993). These reports indicate that cells other than professional antigen presenting cells can be induced to express B7-like molecules. More importantly, that epithelial cells do express a B7-like molecule in some T cell mediated autoimmune states.

The proposed insult that may lead to beta cell B7 expression need not even be beta cell specific. For instance, it has recently been reported that in individuals with IDDM, an immunoglobulin M (IgM) fraction increased L-type calcium channel activity of insulin-producing cells and that the resulting increase in beta cell intracellular calcium resulted in beta cell DNA fragmentation characteristic of programmed cell death (Juntti-Berggren et al., Science, 261:86-90 (1993). Thus, during the active process of programmed cell death, expression of B7 or a similar molecule with costimulatory activity, may be upregulated. The fact that a number of cells express voltage-activated L-type Ca$^{2+}$ channels thus allows for the possibility that an immune reaction initiated in one tissue may indirectly initiate beta cell damage, beta cell B7 expression, and therefore a more specific beta cell immune reaction.

While immunohistologic analysis reveals the presence of CD4$^+$ and CD8$^+$ T lymphocytes, B lymphocytes, and macrophages in the islets of our triple transgenic mice (FIG. 7), it is likely that insulitis was initiated by CD8$^+$ T lymphocytes. The transgenic T cells in our triple transgenic mice are CD8$^+$ and specific for the LCMV-GP in the context of H-2D$^b$ (Ohashi et al., Cell, 65:305-317 (1991); Pircher et al., Nature, 346:629- 633 (1990). It is these transgenic lymphocytes alone with differentiate the GP-B7 mice, which do not develop insulinopenic diabetes, from the GP-B7-TCR mice. Thus, the CD8$^+$ transgenic T cells must themselves be activated when they encounter appropriately presented antigen and a costimulatory signal. Once activated, these CD8$^+$ lymphocytes must initiate processes that result in the recruitment of the other inflammatory cells. Once the lymphocytes are activated, for example, interferon-γ may be produced and thus produce a model similar to transgenic mice expressing that cytokine in beta cells (Sarvetnick et al., Cell, 52:773-782 (1988). The triple transgenic mice are unusual in that such a large proportion of their T cell repertoire is accounted for by the transgenic T cells. In a more typical scenario, CD4$^+$ lymphocytes are probably required to promote the efficient expansion of T cell populations of appropriate antigen specificity.

The literature is replete with reports of transgenic mice which express a variety of gene products in beta cells. Many of these transgenic animals (e.g. those that overexpress MHC class I or aberrantly express MHC class II, H-ras, or chicken calmodulin) develop diabetes but, importantly, display no evidence of immune beta cell destruction (Allison et al., Nature, 333:529-533 (1988); Morahan et al., Nature, 339:622-624 (1989); Sarvetnick et al., Cell, 52:773-782 (1988); Lo et al., Cell, 53:159-168 (1988); Götz et al., Eur. J. Immunol., 20:1677-1683 (1990); Böhme et al., Science, 244:1179-1183 (1989); Efrat, Endocrinology, 128:897-901 (1991); Epstein et al., Cell, 58:1067-1073 (1989). Alternatively, transgenic mice which express other gene products on their pancreatic beta cells (e.g. influenza virus hemagglutinin) display a disrupted islet architecture (Roman et al., Cell, 61:383-396 (1990). Transgenic mice whose islets express certain cytokines (e.g. TNF-α, TNF-β, or IL-2) develop insulitis, but not diabetes (Higuchi et al., J. Exp. Med., 176:1719-1731 (1992); Picarella et al., Proc. Natl. Acad. Sci. USA, 89:10036-10040 (1992); Allison et al., Eur. J. Immunol., 22:1115-1121 (1992). These studies have established several points regarding the use of transgenic models to study autoimmune diabetes. One, as transgenes can affect either islet anatomy or beta cell function, it is necessary to verify normal initial islet morphology and also to demonstrate that any observed diabetes is associated with insulitis and beta cell killing. As shown in FIG. 6, mice transgenic for both beta cell B7 and LCMV GP, or other mice transgenic for both LCMV GP and the LCMV GP-specific TCR, display normal islet structure and immunostaining for insulin. In addition, as none of the LCMV GP-B7 nor the LCMV GP-TCR mice developed diabetes, none the transgenes, either alone or in combination, interfered with the normal expression of insulin. The combination of the three transgenes, however, clearly lead to both insulitis, and beta cell killing (FIG. 5). Two, insulitis is not synonymous with diabetes. Transgenic mice which express TNF-α, TNF-β, or II-2 as well as the recently described NOD strain called NOR (Prochazka et al., Diabetes, 41:98-106 (1992) share the phenotype of insulitis with preserved beta cell function. These data indicate that factors aside from the physical separation of lymphocytes and beta cells contribute to the prevention of immune destruction since the beta cells can co-exist with inflammatory cells. Three, locally produced interferons can induce both insulitis and diabetes. The role of interferons in the pathogenesis of human type I diabetes remains uncertain however since the factors that may induce islet production of interferon-α, or the recruitment of inflammatory cells capable of producing interferon-γ, are unknown. In contrast to other transgenic models of immune mediate diabetes, our triple transgenic mice do not constitutively express any cytokines which may affect immune function in unforeseen ways.

The mechanism of tolerance in the B7-LCMV GP and the previously reported LCMV GP-TCR double transgenic mice may be different. In LCMV GP-TCR double transgenic mice, both immune ignorance and anergy may occur. That is, most of the LCMV GP-TCR mice T lymphocytes may never come in contact with the beta cells (ignorance) and those that do contact the beta cells either fail to achieve an activation threshold (ignorance) or become functionally inactivated (anergized) because they do not receive appropriate costimulatory signals. When LCMV GP-TCR animals are infected with LCMV or vacc-gp, the transgenic T cells not previously anergized (if any) are activated by professional antigen presenting cells and ignorance is broken because activated T cells' binding to endothelial cells is affected allowing more efficient vascular egress and tissue transit (Yednock et al., Adv. Immunol., 44:313–378 (1988); Issekutz, Current Opin. Immunol., 4:287–293 (1992). In the case of the LCMV GP-B7 double transgenic mice, tolerance must be maintained by ignorance alone. While LCMV GP-specific T cells exist in the LCMV GP-B7 mice, as evidenced by the immune mediated beta cell death induced by vacc-gp infection, their precursor frequency must be small. Therefore, while a number of T lymphocytes may pass through the islets, those T cells are statistically unlikely to express receptors with appropriate antigen specificity to be activated. The LCMV GP-B7-TCR triple transgenic mice differ from the LCMV GP-B7 double transgenic mice in that the precursor frequency of antigen-specific T cells is quite high. Consequently, in triple transgenic mice when the migration of a T lymphocyte into a pancreatic islet occurs, the likelihood of that T cell having appropriate antigen specificity is significant, approximately 80%. The triple transgenic mice differ from LCMV GP-TCR double transgenic mice in one important respect, and that is that the LCMV GP-TCR beta cells lack costimulatory molecules. Therefore, when lymphocyte migration into an islet occurs in those mice, even though the likelihood of appropriate antigen specificity is high, the lymphocytes are not activated (and may be anergized) because they do not receive appropriate costimulatory signals. An alternative explanation is that bispecific T cells, as recently described (Brandle et al., Proc. Natl. Acad. Sci. U.S.A., 89:9529–9533 (1992); Borgulya et al., Cell, 69:529–537 (1992); Padovan et al., Science, 262:422–424 (1993) may play a role. In this scenario, T cells expressing two distinct TCRs are cross-activated by environmental antigens via the endogenously rearranged TCR, migrate to the pancreas and cause beta cells destruction via their LCMV GP-specific transgenic TCR. If such T cells bearing two TCRs are playing a role in our model, then since only LCMV GP-B7-TCR developed diabetes spontaneously (LCMV GP-TCR mice never did) it suggests that the B7 on the beta cells must promote an inflammatory process in vivo necessary for the beta cell killing.

"Professional" antigen presenting cells (APC) are characterized by several features. Among them, professional APCs alone express MHC class II molecules under usual circumstances, and they appear to be able to escape the immune mediated death they initiate for other cells presenting identical antigens. It has already been demonstrated however that a variety of cells, including pancreatic beta cells (Pujol-Borrell et al., Nature, 259:974–977 (1987), can be induced to express MHC class II. Further, recent reports suggests that epithelial cells can be induced to express B7 or similar molecules with costimulatory capability (Garcia-Cózar et al., Immunologia, 12:32 (abstract 98) (1993); Nickoloff et al., Am. J. Path., 142:1029–1040 (1993). Taken together, in addition to the now well recognized process of programmed cell death, this indicates that cells may also target themselves for immune destruction by upregulating the expression of MHC class II and/or B7 like molecules.

The results described herein suggest that the regulated absence of B7 or B7-like receptors on the surface of most nonlymphoid cells may be a normal mechanism for the maintenance of T cell tolerance in the periphery. Furthermore, the data illustrates that the aberrant expression of B7 or B7-like molecules on peripheral tissue cells, as has been found in the naturally occurring disease states of Graves' disease (24) and psoriasis (25), can result in a breakdown of T cell unresponsiveness and lead to destructive autoimmune processes.

Other Embodiments

Any species of transgenic animal can be employed as described above, although in some circumstances it may be desirable to use a species, e.g., a primate, such as the rhesus monkey, which is evolutionarily closer to humans than mice. Non-mammals that are subject to autoimmune diseases, e.g., birds such as chickens, can be used as well. Furthermore, any T cell-mediated autoimmune disease can be modeled using the techniques described above, as long as an appropriate tissue-specific promoter is available or designed.

Other embodiments are within the following claims.

Plasmid RIP-B7-IPA was deposited on Jan. 5, 1996 with the American Type Culture Collection, 12301 Parklawn Drive, Rockville, Md., 20852, and assigned the accession number 97412.

We claim:

1. A method for producing a diabetic model for facilitating the screening of therapeutic agents, comprising
manipulating a transgenic rodent such that a diabetic model is produced, wherein the transgenic rodent has a transgene operable in insulin producing cells, said transgene comprising a DNA sequence encoding a B7 polypeptide and a promoter operably linked to said DNA sequence, such that the insulin producing cells express the B7 polypeptide encoded by said transgene.

2. The method of claim 1, wherein the manipulation overcomes immunologic unresponsiveness in the transgenic rodent.

3. The method of claim 2, wherein the manipulation is stimulating a primary immune response in the transgenic rodent.

4. The method of claim 2, wherein the manipulation is inducing an inflammatory response in the transgenic rodent.

5. The method of claim 4, wherein the inflammatory response is induced by administering an agent which induces an inflammatory response in the transgenic rodent.

6. The method of claim 5, wherein the manipulation is administering streptozotocin to the transgenic rodent.

7. The method of claim 6, wherein the streptozotocin is administered in subdiabetogenic doses.

8. The method of claim 2, wherein the manipulation is increasing presentation of antigenic peptides on insulin producing cells of the transgenic rodent.

9. The method of claim 8, wherein increasing presentation of antigenic peptides on insulin producing cells comprises administering an agent which upregulates expression of MHC class II molecules.

10. The method of claim 9, wherein the agent is a cytokine.

11. The method of claim 10, wherein the cytokine is interferon γ.

12. The method of claim 2, wherein the manipulation is inducing islet damage.

13. The method of claim 12, wherein inducing islet damage comprises administering an agent selected from the group consisting of IL-1 and TNF-α.

14. The method of claim 2, wherein the manipulation is treating the transgenic rodent with cyclophosphamide.

15. The method of claim 1, wherein the promoter is an insulin producing cell-specific promoter.

16. The method of claim 15, wherein the insulin producing cell-specific promoter is the rat-1 insulin promoter.

17. The method of claim 1, wherein the B7 polypeptide is a mouse B7 polypeptide.

18. The method of claim 1, wherein the transgene is contained in plasmid RIP-B7-IpA (ATCC Designation No. 97412).

19. The method of claim 18, wherein the transgene is a section of plasmid RIP-B7-IpA (ATCC Designation No. 97412) between restriction sites Sst I and Stu I.

* * * * *